US008017384B2

(12) United States Patent
Tsai et al.

(10) Patent No.: US 8,017,384 B2
(45) Date of Patent: Sep. 13, 2011

(54) MODULAR MEMBRANE SUPPORTED BIOREACTOR FOR CONVERSION OF SYNGAS COMPONENTS TO LIQUID PRODUCTS

(75) Inventors: Shih-Perng Tsai, Naperville, IL (US); Rathin Datta, Chicago, IL (US); Rahul Basu, Naperville, IL (US); Seong-Hoon Yoon, Naperville, IL (US); Richard E. Tobey, St. Charles, IL (US)

(73) Assignee: Caliper Life Sciences, Inc., Mountain View, CA (US)

( * ) Notice: Subject to any disclaimer, the term of this patent is extended or adjusted under 35 U.S.C. 154(b) by 402 days.

(21) Appl. No.: 12/111,734

(22) Filed: Apr. 29, 2008

(65) Prior Publication Data
US 2009/0029434 A1    Jan. 29, 2009

Related U.S. Application Data

(63) Continuation-in-part of application No. 11/781,717, filed on Jul. 23, 2007, now abandoned.

(51) Int. Cl.
*C12M 1/12* (2006.01)
(52) U.S. Cl. .......... 435/297.4; 435/289.1; 435/297.1; 435/297.2; 435/297.3; 435/297.5
(58) Field of Classification Search ............ 435/289.1, 435/297.1–297.5
See application file for complete search history.

(56) References Cited

U.S. PATENT DOCUMENTS

| 3,993,816 | A | * | 11/1976 | Baudet et al. ............... 428/45 |
| 4,181,604 | A |   | 1/1980  | Onishi et al. |
| 4,746,435 | A |   | 5/1988  | Onishi et al. |
| 5,106,506 | A |   | 4/1992  | Schmidt et al. |
| 5,173,429 | A |   | 12/1992 | Gaddy et al. |
| 5,753,474 | A |   | 5/1998  | Ramey |
| 5,851,267 | A |   | 12/1998 | Schwartz |
| 5,938,922 | A | * | 8/1999  | Fulk et al. ................ 210/321.81 |
| 6,043,392 | A |   | 3/2000  | Holtzapple et al. |
| 6,136,577 | A |   | 10/2000 | Gaddy |

(Continued)

FOREIGN PATENT DOCUMENTS
WO    WO 02/08438    1/2002

OTHER PUBLICATIONS

"Evidence for Production of n-Butanol from Carbon Monoxide by *Butyribacterium methylotrophicum*," Journal of Fermentation and Bioengineering, vol. 72, 1991, p. 58-60.

(Continued)

*Primary Examiner* — Michael Marcheschi
*Assistant Examiner* — Jameson Ma
(74) *Attorney, Agent, or Firm* — Cardinal Law Group

(57) ABSTRACT

A modular membrane supported bioreactor for anaerobic conversion of gas into liquid products including membrane module(s) having a plurality of hollow fibers packed across a cross sectional area of the membrane module in a direction transverse to the axis of the membrane module; a membrane vessel for retaining the membrane module(s) at least partially submerged in a process liquid and isolated from ambient atmosphere; and a gas supply conduit operably connected to the hollow fibers for supplying a process gas to the hollow fiber lumens. The gas supply conduit enables the formation of a biofilm on the outer surface of the hollow fiber wall by interaction of microorganisms with the process gas and the production of a liquid product that mixes with the process liquid.

11 Claims, 12 Drawing Sheets

U.S. PATENT DOCUMENTS

| | | | |
|---|---|---|---|
| 6,228,607 B1 * | 5/2001 | Kersten et al. | 435/41 |
| 6,387,262 B1 | 5/2002 | Rittmann et al. | |
| 6,558,549 B2 | 5/2003 | Cote et al. | |
| 6,755,975 B2 | 6/2004 | Vane et al. | |
| 6,844,187 B1 * | 1/2005 | Wechsler et al. | 435/297.2 |
| 6,899,743 B2 | 5/2005 | Wijmans et al. | |
| 6,908,547 B2 | 6/2005 | Cote et al. | |
| 6,919,488 B2 | 7/2005 | Melnichuk et al. | |
| 7,118,672 B2 | 10/2006 | Husain et al. | |
| 7,169,295 B2 | 1/2007 | Husain et al. | |
| 7,189,323 B2 | 3/2007 | Lofqvist et al. | |
| 7,704,723 B2 | 4/2010 | Huhnke et al. | |
| 2003/0211585 A1 * | 11/2003 | Gaddy et al. | 435/161 |
| 2005/0054087 A1 | 3/2005 | Cote et al. | |
| 2005/0082227 A1 * | 4/2005 | Cote et al. | 210/650 |
| 2005/0260739 A1 * | 11/2005 | Rosen et al. | 435/254.21 |
| 2006/0014274 A1 * | 1/2006 | Klaus | 435/297.4 |
| 2006/0021936 A1 | 2/2006 | Husain et al. | |
| 2006/0037896 A1 | 2/2006 | Cote et al. | |
| 2006/0163157 A1 | 7/2006 | Cote et al. | |
| 2007/0056893 A1 * | 3/2007 | Noh et al. | 210/321.61 |
| 2007/0275447 A1 | 11/2007 | Lewis et al. | |
| 2008/0305539 A1 | 12/2008 | Hickey et al. | |
| 2008/0305540 A1 | 12/2008 | Hickey et al. | |
| 2009/0035848 A1 | 2/2009 | Hickey | |
| 2009/0215139 A1 | 8/2009 | Datta et al. | |
| 2009/0215163 A1 | 8/2009 | Tsai et al. | |
| 2010/0105116 A1 | 4/2010 | Datta et al. | |

OTHER PUBLICATIONS

"Production of butanol and ethanol from synthesis gas via fermentation," FUEL, vol. 70, May 1991, p. 615-619.

Das, A. and L.G. Ljungdahl, Electron Transport Systems in Acetogens, Chapter 14, in Biochemistry and Physiology of Anaerobic Bacteria, L.G. Ljungdahl et al eds., Springer (2003).

Drake, H.L. and K. Kusel, Diverse Physiologic Potential of Acetogens, Chapter 13, in Biochemistry and Physiology of Anaerobic Bacteria, L.G. Ljungdahl et al eds., Springer (2003).

Muller, V., Minireview: Energy Conservation in Acetogenic Bacteria, Applied and Environmental Microbiology, vol. 69, 11, 6345-53, Nov. 2003.

Innovations in Wastewater Treatment: The moving bed biofilm process. Water Science and Technology vol. 53 No. 9 pp. 17-33.

Rahtin Datta and J.G. Zeikus, Anaerobic Conversion of One-Carbon Compounds. vol. 24 of Developments in Industrial Microbiology, 1983.

Popular Mechanics, Coskata Ethanol Technology—How it Works—Illustration and Analysis, http://www.popularmechanics.com/science/research/4248759.html?series=19, Feb. 22, 2008, pp. 1-3.

Ethanol Production by Saccharomyces cerevisiae Immobilized in Hollow-Fiber Membrane Bioreactors, Douglas S. Inloes, et al., Applied and Environmental Microbiology, Jul. 1983, pp. 264-278, vol. 46. No. 1.

* cited by examiner

MODULAR MEMBRANE SUPPORTED BIOREACTOR FOR CONVERSION OF SYNGAS COMPONENTS TO LIQUID PRODUCTS

CROSS REFERENCE TO RELATED APPLICATIONS

This application claims priority, and the benefit, as a continuation in part from U.S. patent application Ser. No. 11/781,717, filed Jul. 23, 2007, now abandoned, incorporated herein in its entirety by reference.

FIELD OF THE INVENTION

This invention relates to the biological conversion of CO and mixtures of $CO_2$ and $H_2$ to liquid products in bioreactors.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol, hexanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas or syngas components can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

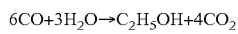

$$6CO + 3H_2O \rightarrow C_2H_5OH + 4CO_2$$

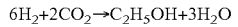

$$6H_2 + 2CO_2 \rightarrow C_2H_5OH + 3H_2O$$

Thus, 6 moles of relatively insoluble gases such as CO or $H_2$ have to transfer to an aqueous medium for each mole of ethanol. Other products such as acetic acid and n-butanol have similar large stoichiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance.

Many devices and equipment are used for gas transfer to microorganisms in fermentation and waste treatment applications. These numerous bioreactors all suffer from various drawbacks. In most of these conventional bioreactors and systems, agitators with specialized blades or configurations are used. In some others such as gas lift or fluidized beds, liquids or gases are circulated via contacting devices. The agitated vessels require a lot of mechanical power often in the range of 4 to 10 KW per 1000 gallons—uneconomical and unwieldy for large scale fermentations that will be required for such syngas bioconversions. The fluidized or fluid circulating systems cannot provide the required gas dissolution rates. Furthermore, most of these reactors or systems are configured for use with microorganisms in planktonic form i.e. they exist as individual cells in liquid medium.

To get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters.

Cell retention by formation of biofilms is a very good and often inexpensive way to increase the density of microorganisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

Particular forms of membranes have found use in supporting specific types microorganisms for wastewater treatment processes. U.S. Pat. No. 4,181,604 discloses the use of hollow fiber membranes for waste treatment where the outer surface of the fibers supports a layer of microorganisms for aerobic digestion of sludge.

Existing bioreactors are either small scale, unsuitable for large scale manufacturing processes, or custom designed, increasing manufacturing and installation costs. The costs of membrane housings and piping can be a significant addition to the cost of the membrane itself. Bioreactors have been unable to take advantage of standardized configurations and hardware that would improve the plant economics.

It would be desirable to have a modular membrane supported bioreactor and method of use that would overcome the above disadvantages.

SUMMARY OF THE INVENTION

It has been found that contacting syngas components such as CO or a mixture of $CO_2$ and $H_2$ with a surface of a membrane and transferring these components in contact with a biofilm on the opposite side of the membrane will provide a stable system for producing liquid products such as ethanol, butanol, hexanol and other chemicals and that these systems can be put into standard module arrangements. Accordingly this invention is a membrane supported bioreactor system for conversion of syngas components such as CO, $CO_2$ and $H_2$ to liquid fuels and chemicals by anaerobic micorooganisms supported on the surface of membrane in a readily available module configuration. The gas fed on the membrane's gas contact side transports through the membrane to a biofilm of the anaerobic microorganisms where it is converted to the desired liquid products.

The instant invention uses microporous membranes or non-porous membranes or membranes having similar properties that transfer (dissolve) gases into liquids for delivering the components in the syngas directly to the cells that use the CO and $H_2$ in the gas and transform them into ethanol and other soluble products. The membranes concurrently serve as the support upon which the fermenting cells grow as a biofilm and are thus retained in a concentrated layer. The result is a highly efficient and economical transfer of the syngas at essentially 100% dissolution and utilization, overcoming limitations for the other fermentation methods and fermenter configurations. The syngas diffuses through the membrane from the gas side and into the biofilm where it is transformed by the microbes to the soluble product of interest. Liquid is passed in the liquid side of the membranes via pumping, stirring or similar means to remove the ethanol and other soluble products formed; the products are recovered via a variety of suitable methods.

A broad embodiment of this invention is a bioreactor system for converting a feed gas containing at least one of CO or a mixture of $CO_2$ and $H_2$ to a liquid product. The system comprises a bio-support membrane having a gas contacting side in contact with the feed gas for transferring said feed gas across the membrane to a biofilm support side for supporting a microorganism that produces a liquid product. The feed gas supply conduit delivers feed gas to the membrane system through a feed gas chamber having fluid communication with the gas supply conduit and the gas contact side of the membrane for supplying feed gas to the membrane. A liquid retention chamber in fluid communication with the biofilm support side of the membrane receives liquid products and a liquid recovery conduit in fluid communication with the liquid recovery chamber recovers a liquid product from the membrane system.

An additional embodiment of the instant invention includes the supply of dissolved syngas in the liquid phase to the side of the biofilm in contact with that phase. This allows dissolved gas substrate to penetrate from both sides of the biofilm and maintains the concentration within the biofilm at higher levels allowing improved reaction rates compared to just supplying the syngas via the membrane alone. This may be accomplished by pumping a liquid stream where the gases are predissolved into the liquid or by pumping a mixture of liquid containing the syngas present as small bubbles using fine bubble diffusers, jet diffusers or other similar equipment commonly used to transfer gas into liquids. The potential added advantage of using the combined gas and liquid stream is that the additional shear produced by the gas/liquid mixture may be beneficial in controlling the thickness of the biofilm. The advantage of pre-dissolution of the syngas is that very little, if any, of the gas is lost from the system so utilization efficiency is maximized.

Another embodiment of this invention includes the preferential removal of the carbon dioxide ($CO_2$) gas that is formed in the bioconversion process from the syngas using a membrane that selectively permeates $CO_2$ and then returning the syngas enriched in CO and $H_2$ to the bioreactor.

A further embodiment of this invention is a modular membrane bioreactor for the anaerobic conversion of gas into liquid products. The bioreactor includes at least one membrane module having a plurality of hollow fibers, each of the plurality of hollow fibers having a gas permeable hollow fiber wall defining a hollow fiber lumen and an outer surface. The hollow fibers are packed across a cross sectional area of the membrane module in a direction transverse to the axis of the membrane module. A gas supply conduit is operably connected to the hollow fibers for supplying a process gas to the hollow fiber lumens. A membrane vessel is arranged to retain membrane modules at least partially submerged in a process liquid for the formation of a biofilm on the outer surface of the hollow fiber wall by interaction of microorganisms with the process gas. The membrane vessel has a transverse cross sectional area of no more than 1.5 times the cross sectional area of the membrane module. The bioreactor also enables interaction of microorganisms with the process gas to produce a liquid product that mixes with the process liquid.

In a more specific embodiment the membrane bioreactor is for the anaerobic conversion of syngas into liquid products. The membrane bioreactor includes a plurality of membrane modules stacked in an axial direction. Each membrane module has a plurality of hollow fibers, each of the plurality of hollow fibers having a gas permeable hollow fiber wall defining a hollow fiber lumen and an outer surface. A gas supply conduit is operably connected to the hollow fibers for supplying a process gas containing at least one of CO or a mixture of $CO_2$ and $H_2$ to the hollow fiber lumens. A membrane vessel retains the membrane modules at least partially submerged in a process liquid and above atmospheric pressure for the formation of a biofilm containing microorganisms selected from the group consisting of *Clostridium ragsdalei, Butyribacterium methylotrophicum, Clostridium ljungdahlii, Clostridium carboxidivorans*, and combinations thereof on the outer surface of the hollow fiber wall. The bioreactor enables interaction of the biofilm with the process gas for the production of a liquid product selected from the group consisting of ethanol, n-butanol, hexanol, acetic acid, butyric acid, and combinations thereof that mixes with the process liquid.

In a method embodiment this invention is a bioreaction method that retains a process liquid in a membrane vessel under anaerobic conditions. A membrane module is maintained at least partially submerged in the process liquid, the membrane module having a plurality of hollow fibers, each of the plurality of hollow fibers having a hollow fiber wall defining a hollow fiber lumen and an outer surface. The method grows a biofilm on the outer surface of the hollow fibers and passes a process gas into the hollow fiber lumens and through the hollow fiber wall and interacts the gas with the biofilm to generate a liquid product that mixes with the process liquid.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE INVENTION

Figure 1:
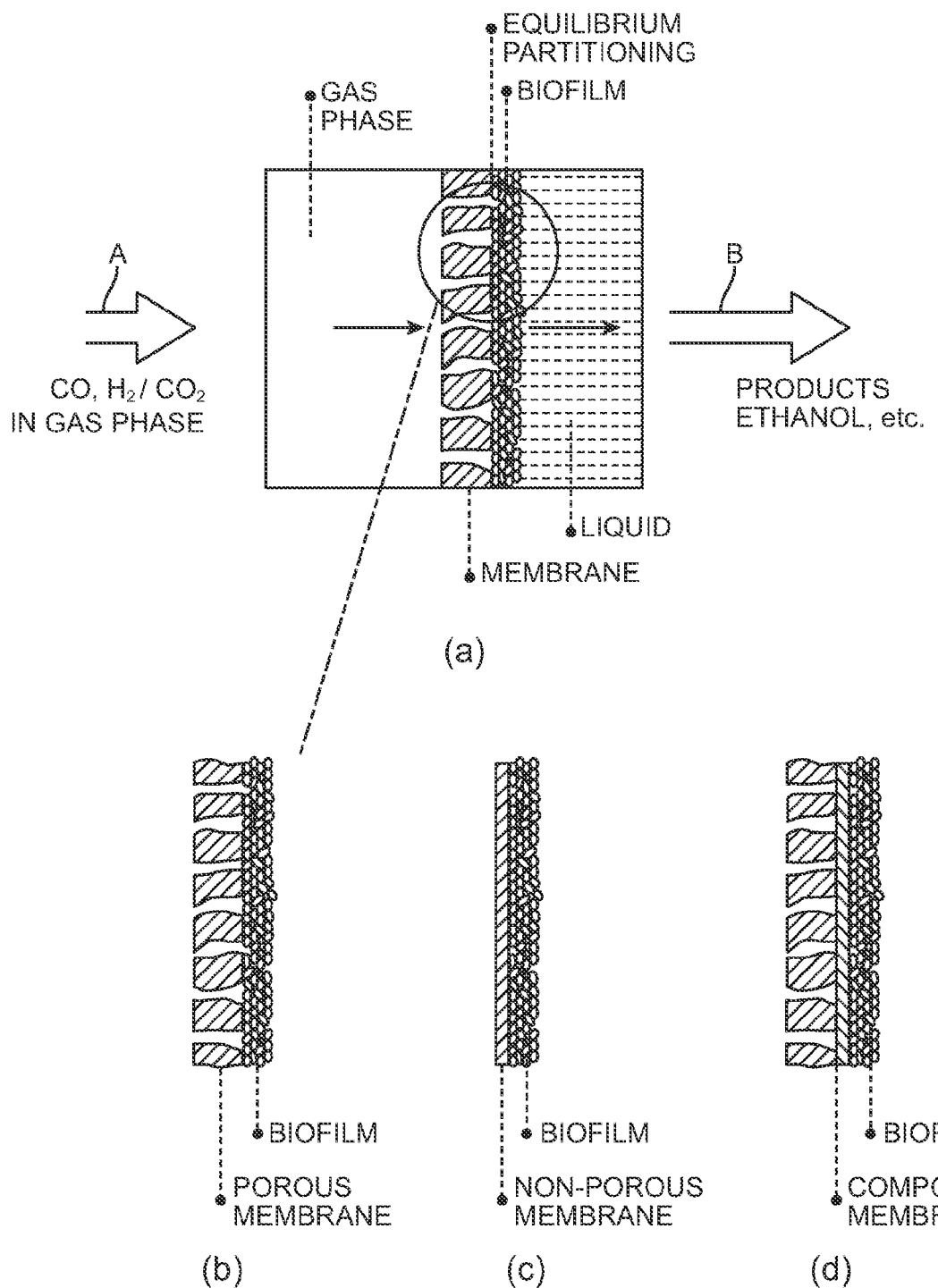
FIG. 1 is a schematic drawing showing gas diffusing through a porous membrane into a liquid and details of a porous membrane, non-porous membrane and composite membrane.

Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol, n-butanol and/or hexanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahlii*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid. All of these references are incorporated herein in their entirety.

The microorganisms found suitable thus far for this invention require anaerobic growth conditions. Therefore the system will employ suitable control and sealing methods to limit the introduction of oxygen into the system. Since the organisms reside principally in contact with the liquid volume of the retention chamber the system maintains a suitable redox potential in the liquid and this chamber may be monitored to make insure anaerobic conditions. Anaerobic conditions in the retained liquid volume are usually defined as having a redox potential of less than −200 mV and preferably a redox potential in the range of from −300 to −500 mV. To further minimize exposure of the microorganisms to oxygen the feed gas will preferably have an oxygen concentration of less than 1000 ppm, more preferably less than 100 ppm, and even more preferably less than 10 ppm.

The instant invention uses microporous membranes or non-porous membranes or membranes having similar properties in being able to transfer (dissolve) gases into liquids for delivering the components in the syngas directly to the cells that use the CO and $H_2$ in the gas and transform them into ethanol and other soluble products. The membranes concurrently serve as the support upon which the fermenting cells grow as a biofilm and are thus retained in a concentrated layer. The result is a highly efficient and economical transfer of the syngas at essentially 100% dissolution and utilization, overcoming limitations for the other fermentation methods and fermenter configurations. The syngas diffuses through the membrane from the gas side and into the biofilm where it is transformed by the microbes to the soluble product of interest. Liquid is passed in the liquid side of the membranes via pumping, stirring or similar means to remove the ethanol and other soluble products formed; the products are recovered via a variety of suitable methods.

Microporous membranes made from polymers or ceramics have been recently developed and commercialized for wastewater treatment and purification applications. Some variations of these have also been developed for aeration or oxygenation of liquids. Typically these membranes are made from hydrophobic polymers such as polyethylene or polypropylene which are processed to create a fine porous structure in the polymer film. Many commercial organizations supply such membranes primarily in two important geometries—hollow fiber and flat sheets. These can then be made into modules by appropriate potting and fitting and these modules have very high surface area of pores in small volumes.

Suitable hydrophobic microporous hollow fiber membranes have been used for degassing applications to remove oxygen, carbon dioxide, and other gases from water and other liquids. An example of commercial membrane modules for such applications is the Liqui-Cel® membrane contactor from Membrana (Charlotte, N.C.), containing the polypropylene (PP) X40 or X50 hollow fibers. CELGARD® microporous PP hollow fiber membrane, containing the X30 fibers, is also available from Membrana for oxygenation applications. Liqui-Cel® membrane modules suitable for large scale industrial applications have large membrane surface areas (e.g., 220 m² active membrane surface area for Liqui-Cel® Industrial 14×28). Some characteristics of these fibers are given in the Table 1 below.

TABLE 1

|  | X30 | X40 | X50 |
|---|---|---|---|
| Porosity (nominal) | 40% | 25% | 40% |
| Pore Size | 0.03 μm | 0.04 μm | 0.04 μm |
| Internal Diameter | 240 μm | 200 μm | 220 μm |
| Outer Diameter | 300 μm | 300 μm | 300 μm |
| Wall Thickness | 30 μm | 50 μm | 40 μm |

A microporous PP hollow fiber membrane product (Cell-Gas® module) is available from Spectrum Laboratories (Rancho Dominguez, Calif.) for gentle oxygenation of bioreactors without excessive shear to the microbial or cell cultures. This PP hollow fiber is hydrophobic, with a nominal pore size of 0.05 μm and a fiber inner diameter of 0.2 mm.

For the use of hydrophobic microporous membranes for afore-mentioned applications, it is necessary to properly manage the pressure difference across the membrane to avoid formation of bubbles in the liquid. If the pressure difference is greater than a critical pressure, the value of which depends on properties of the liquid and the membrane, liquid can enter the pore ("wetting") and the gas transfer rate is significantly impeded.

To prevent wetting of pores during operations, some composite membranes have been developed by the membrane suppliers. The SuperPhobic® membrane contactor from Membrana keeps the gas phase and liquid phase independent by placing a physical barrier in the form of a gas-permeable non-porous membrane layer on the membrane surface that contacts the process liquid. The SuperPhobic® 4×28 module contains 21.7 m² membrane surface area. Another composite hollow fiber membrane with an ultra-thin nonporous membrane sandwiched between two porous membranes is available from Mitsubishi Rayon (Model MHF3504) in the form of composite hollow fibers having at 34 m² membrane area per module.

Non-porous (dense) polymeric membranes have been used commercially for various gas separation applications. These membranes separate gases by the selective permeation across the membrane wall. The solubility in the membrane material and the rate of diffusion through the molecular free volume in the membrane wall determine its permeation rate for each gas. Gases that exhibit high solubility in the membranes and gasses that are small in molecular size permeate faster than larger, less soluble gases. Therefore, the desired gas separation is achieved by using membranes with suitable selectivity in conjunction with appropriate operating conditions. For example, Hydrogen Membranes from Medal (Newport, Del.) are used in recovery or purification of hydrogen with preferential permeation of hydrogen and $CO_2$. Medal also provides membranes for $CO_2$ removal with preferential permeation of $CO_2$.

In addition, composite membranes having a thin nonporous silicone layer on the surface of polypropylene microporous hollow fibers have been fabricated by Applied Membrane Technology, Inc. (Minnetonka, Minn.) and Senko Medical Instrument Manufacturing (Tokyo, Japan) and evaluated for artificial lung applications. See "Evaluation of Plasma Resistant Hollow Fiber Membranes for Artificial Lungs" by Heide J. Eash et al. ASAIO Journal, 50(5): 491-497 (2004).

Microporous membranes have been used widely in membrane bioreactors for wastewater treatment. Installations are mostly in the submerged membrane configuration using hollow fiber or flat sheet membranes for wastewater treatment. The structure and module configuration of these membranes may prove particularly useful for the systems of this invention. The membranes are typically made of poly(vinylidene fluoride) (PVDF), polyethylene (PE), PP, poly(vinyl chloride) (PVC), or other polymeric materials. The typical pore size is in the range of 0.03 to 0.4 μm. The typical hollow fiber outer diameter is 0.5 to 2.8 mm and inner diameter 0.3 to 1.2 mm. In these submerged membrane configurations, wastewater containing contaminants are fed into a tank and treated water is filtered through the membrane with a suction pressure applied to the filtrate side (the lumen side of the hollow fiber or the center of the flat plate) of the membrane. Typically the tank retains multiple membrane modules submerged without an individual housing. There are a number of commercial suppliers of membranes for submerged membrane bioreactors in wastewater treatment, each with some distinct features in membrane geometry and module design as described below. These membrane geometries and module designs can be suitable for the instant invention and are incorporated herein.

For wastewater treatment and biomedical applications in which efficient transfer of oxygen into an aqueous phase is desired, hollow fiber membranes made of polymethylpentene (PMP) have been used, due to the high permeability of PMP for oxygen. These PMP hollow fibers are non-porous and of either the skinned asymmetric or dense type as described in "Evaluation of Plasma Resistant Hollow Fiber Membranes for Artificial Lungs" by Heide J. Eash et al. ASAIO Journal, 50(5): 491-497 (2004) and U.S. Pat. No. 7,118,672 B2.

A hollow fiber membrane SteraporeSUN™, available from Mistubishi Rayon (Tokyo, Japan), is made of PE with modified hydrophilic membrane surface. The hollow fiber has a nominal pore size of 0.4 μm and a fiber outer diameter of 0.54 mm. A SteraporeSUN™ membrane unit Model SUN21034LAN has a total membrane surface area of 210 m², containing 70 membrane elements Model SUR334LA, each with 3 m² membrane area.

Another hollow fiber membrane SteraporeSADF™ is available from Mitsubishi Rayon. This membrane is made of PVDF with a nominal pore size of 0.4 μm and a fiber outer diameter of 2.8 mm. Each SteraporeSADF™ membrane element Model SADF2590 contains 25 m² membrane surface area, and each StreraporeSADF™ membrane unit Model SA50090APE06 containing 20 SADF2590 membrane elements has a total membrane surface area of 500 m².

Other commercial microporous hollow fiber membranes used for membrane bioreactors include but are not limited to the Zenon ZeeWeed® membranes from GE Water & Process Technologies (Oakville, Ontario, Canada), the Puron® membranes from Koch Membrane Systems (Wilmington, Mass.), and the MemJet® membranes from Siemens Water Technologies (Warrendale, Pa.).

Kubota Corporation (Tokyo, Japan) markets submerged membrane systems for membrane bioreactors. These membranes are of the flat-plate configuration and made of PVC with a pore size of 0.4 µm. Each membrane cartridge has 0.8 m² membrane surface area, and a Model EK-400 membrane unit, containing 400 membrane cartridges, has a total membrane area of 320 m².

Membranes of the various geometries and compositions described above may be used in arrangements of unitary arrays or assemblies of varied composition in the systems of this invention. Thus bio-support membrane used in the instant invention can be microporous, non-porous, or composite membranes or any combination thereof. Any suitable potting technique can be used to collect and provide the necessary assembly of individual membrane elements. If microporous, hydrophobic membranes are preferred due to faster diffusion of gases in the gas-filled pores than liquid-filled pores.

The feed gas flows through the gas chamber of the membrane unit continuously or intermittently. The feed gas pressure is in the range of 1 to 1000 psia, preferably 5 to 400 psia, and most preferably 10 to 200 psia. Operating at higher gas pressures has the advantage of increasing the solubilities of gases in the liquid and potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained.

In such membranes the gas and liquid can be brought into direct and intimate contact without creating any bubbles by operating at a differential pressure that is below the bubble point of the membrane liquid interface and maintains the gas-liquid interface. Furthermore, the properties of this interface can be controlled by the porosity and hydrophobicity/hydrophlicity properties of the membrane pores.

In this invention, a bio-support membrane suitable for permeation of at least one of CO or a mixture of $H_2$ and $CO_2$ provides the separation between a feed gas and a liquid phase. FIG. 1 shows more detail of the membrane configuration and interface in the operation of a representative bio-reactor system. FIG. 1(a) depicts syngas stream A flowing to the gas feed side of the membrane in gas phase maintained in a chamber on the gas contact side of the membrane. The syngas components freely diffuse through the membrane pores to the liquid interface but without formation of bubbles. The anaerobic acetogenic bacteria, *Clostridium ragsdaeli*, having all of the identifying characteristics of ATCC No. BAA-622, is maintained in a fermentation media. The fermentation media is circulated through a chamber on the opposite side of the membrane that maintains a liquid volume in contact with the liquid side of the membrane. Suitable microbial cells are present as bio-film on the liquid-contacting side of the membrane surface, converting at least one of CO or $H_2/CO_2$ in the feed gas to desirable products. Since the membrane pores are much smaller than the width of the microorganisms they preferentially stay on the membrane surface to convert CO and $H_2/CO_2$ to gain metabolic energy, grow and form a biofilm on the membrane surface. A stream B withdraws the liquid phase components from a liquid volume retained about the outer surface of the biofilm.

FIGS. 1(b)-(c) show various forms of the membrane with a biofilm present on the liquid contacting side of the membrane. The membrane portions of FIGS. 1(a) and 1(b) both schematically show a cross-section of porous membrane to the left with a biofilm layer developed on the opposite side of the membrane. The interface between the biofilm and the membrane functions as equilibrium partitioning to keep the liquid and gas phases separated from each other. FIG. 1(c) depicts a similar arrangement however this time with a nonporous membrane to the left and a biofilm adhering to the surface on the right-hand side of the membrane. FIG. 1(d) illustrates a composite structure for the membrane that positions a porous membrane surface in contact with the gas phase components. The opposite face (right side) of the porous membrane retains a nonporous membrane layer and a biofilm layer adheres to the surface on the right side of the non-porous membrane layer.

Figure 2:
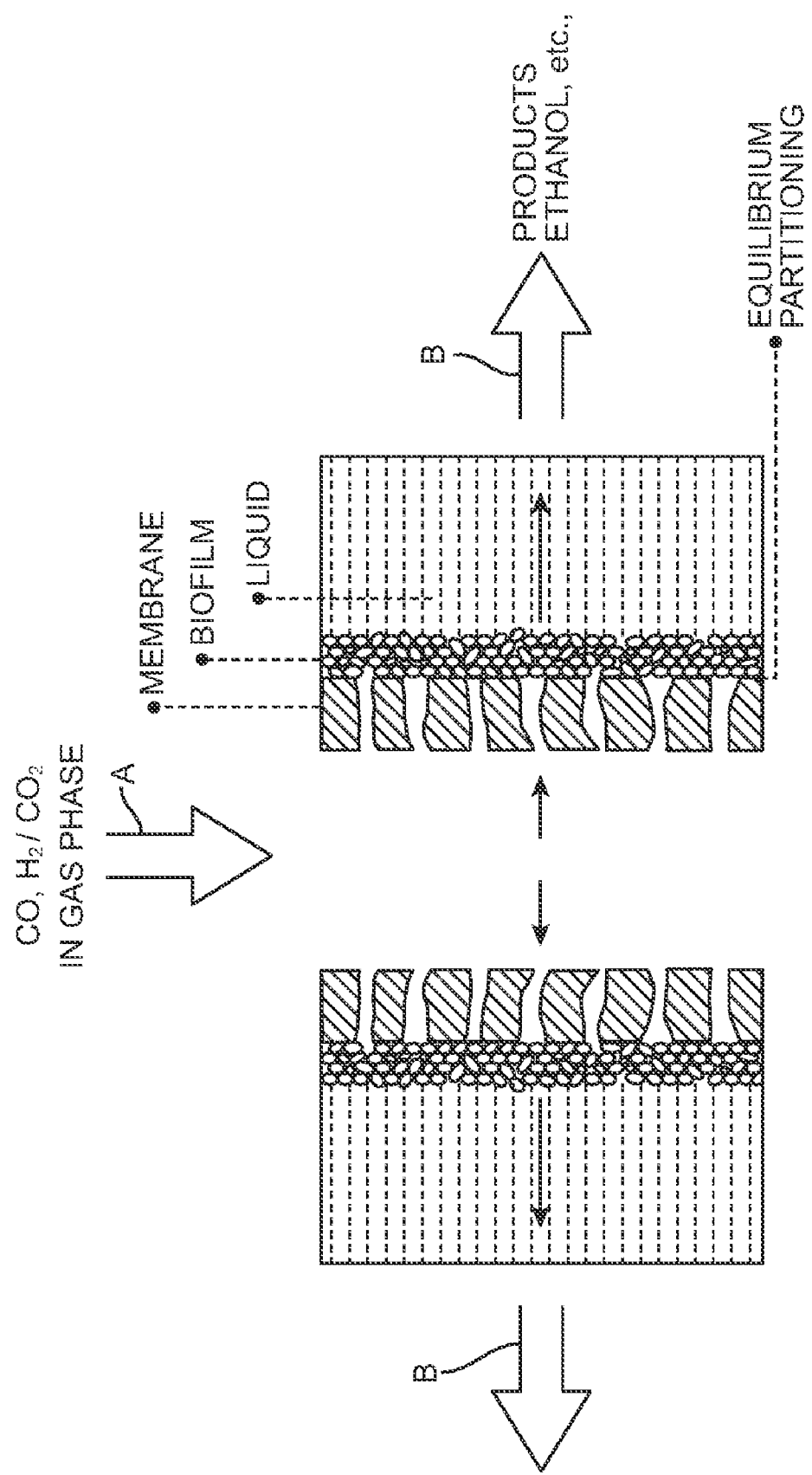
FIG. 2 is a schematic drawing showing a central passage delivering gas to two parallel membrane walls with a liquid phase to the outside of each wall.

FIG. 2 depicts a generalized view of a typical flow arrangement for efficient use of space in a membrane system. Syngas components enter the system as gas stream A and flow into a central space between two membrane walls. Gas phase contact surfaces of the opposing membrane walls form a distribution chamber for receiving gas from stream A. Gas permeates simultaneous through, in this case, the porous membrane for consumption by the microbes in the biofilm layers that adhere to the outer walls of the two opposing membranes. In this manner each gas channel serves multiple membrane surfaces and the stream B of liquid products is delivered from multiple membrane walls. The arrangement of FIG. 2 can use a flat sheet configuration and be particularly useful for good flow control and distribution on the liquid side that may be necessary for biofilm thickness control.

Figure 3:
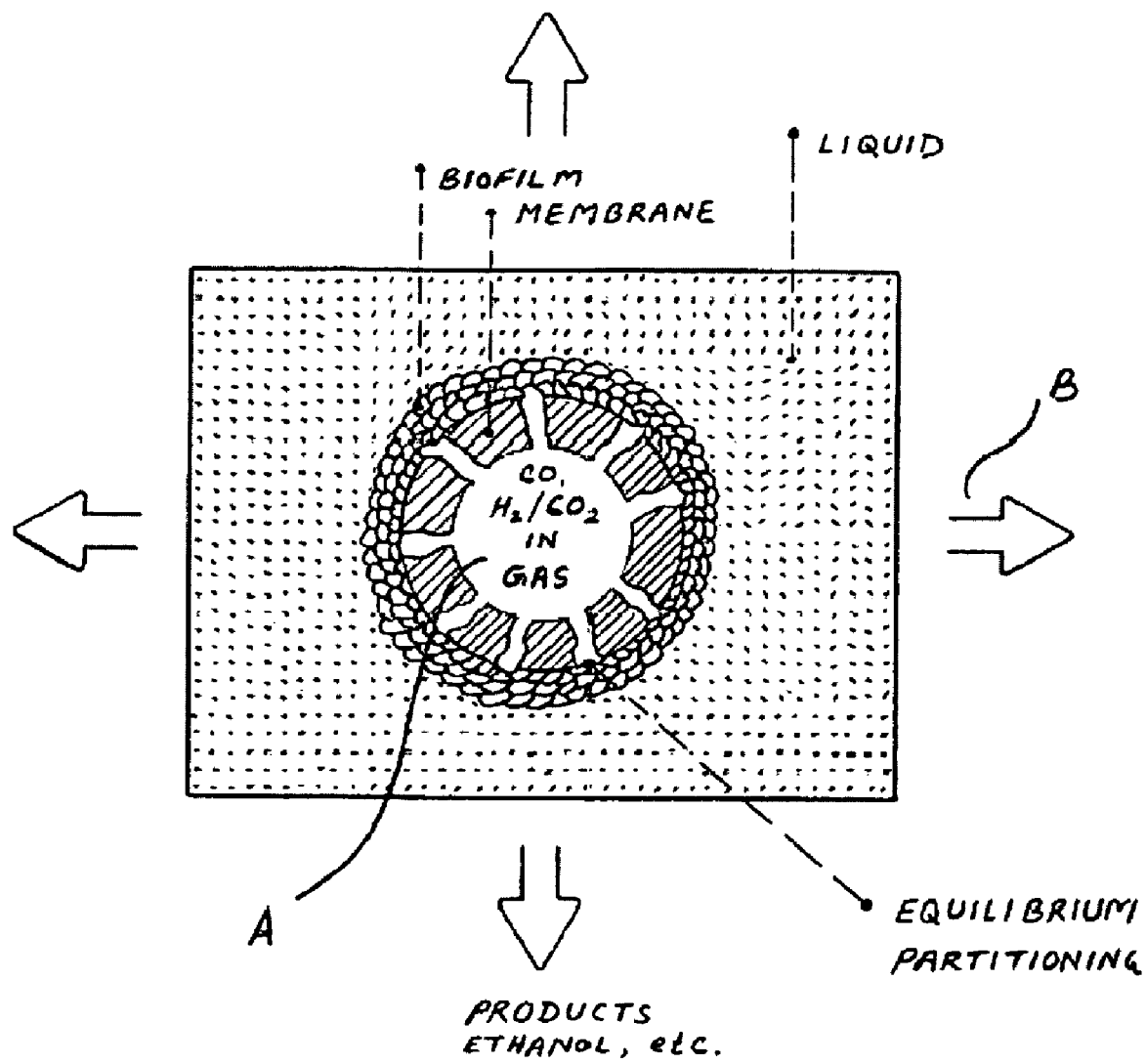
FIG. 3 is a schematic drawing showing the interior passage of FIG. 2 enclosed by the interior surface of the membrane in tubular form with liquid retained to around the membrane circumference.

FIG. 3 shows the special case of FIG. 2 wherein the opposite wall of the central distribution chamber wrap around in continuous form to provide a tubular membrane. In this case gas stream A enters the lumen of the membrane and streams B of liquid products flow away from the outer walls in all directions. Hollow fibers are particularly useful for such bioreactor configuration.

Figure 4:
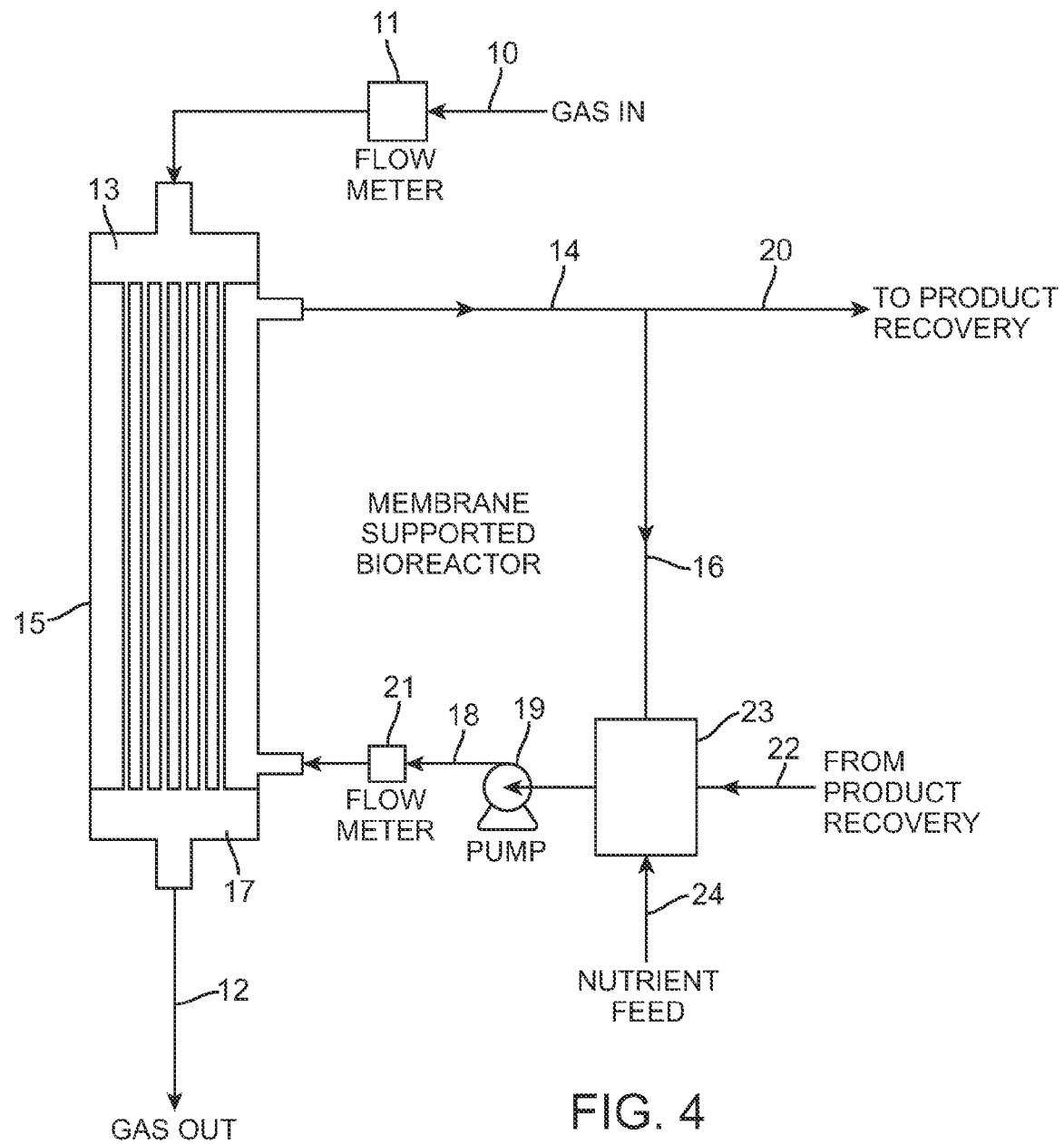
FIG. 4 is a schematic drawing showing a bioreactor system with gas and liquid circulation.

FIG. 4 illustrates a specific configuration of one embodiment of this invention. A gas supply conduit delivers a feed gas stream 10 containing CO, $H_2$, and $CO_2$ at a rate recorded by a flow meter 11. A feed gas distribution chamber 13 receives the feed gas stream and distributes the feed to the lumens of tubular membranes in a membrane unit 15 that provides a membrane supported bioreactor. A collection chamber 17 collects a portion of the feed gas that exits the lumens and an exhaust gas stream 12 from chamber 17 exits the membrane unit.

A vessel or tank surrounds the outside of the tubular membrane elements in the membrane supported bioreactor and retains a liquid for growth and maintenance of a biofilm layer on the outer surface of the membrane. The tank provides the means of temperature and pH controls for the liquid, which contains nutrients needed to sustain the activity of the microbial cells. The liquid in the tank is stirred to provide adequate mixing and sparged with a suitable gas, if necessary, to maintain a suitable gaseous environment. A re-circulating liquid loop, consisting of Streams 14, 16, and 18 re-circulates liquid through the tank. Liquid flows from the tank through lines 14 and 16 while line 20 withdraws liquid and takes to product recovery to recover liquid products. Line 18 returns the remaining liquid from line 16 to the tank via pump 19 at rate recorded by flow meter 21. The product recovery step removes the desirable product from Stream 20, while leaving substantial amounts of water and residual nutrients in the treated stream, part of which is returned to the bioreactor system via line 22. A nutrient feed is added via line 24 is added, as needed, to compensate for the amount of water removed and to replenish nutrients. Chamber 23 provides any mixing of the various streams and for return to the tank via line 18.

The flow rates of Streams 18 and 14, recirculated through the membrane unit, are selected so that there is no significant liquid boundary layer that impedes mass transfer near the liquid-facing side of the membrane and there is no excessive shear that may severely limit the attachment of cells and formation of the biofilm on the membrane surface. The superficial linear velocity of the liquid tangential to the membrane should be in the range of 0.01 to 20 cm/s, preferably 0.05 to 5 cm/s, and most preferably 0.2 to 1.0 cm/s. In addition to the liquid linear velocity, the biofilm thickness can be controlled by other means to create shear on the liquid-biofilm interface, including scouring of the external membrane surface with gas bubbles and free movement of the hollow fibers. Also, operating conditions that affect the metabolic activity of the microbial cells and the mass transfer rates of gases and nutrients can be manipulated to control the biofilm thickness. The biofilm thickness in the instant invention is in the range of 5-500 μm, preferably 5-200 μm.

Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products.

In all the depicted arrangement the CO an $H_2$ from the syngas are utilized and a gradient for their transport from the gas feed side is created due to biochemical reaction on the membrane liquid interface. This reaction creates liquid fuel or chemicals such as ethanol and acetic acid which diffuse into the liquid and are removed via circulation of the liquid past the biofilm. Thus the very large surface areas of the membrane pores are usable for gas transfer to the biofilm and the product is recovered from the liquid side. Furthermore, the reaction rate, gas concentration gradient and the thickness of the biofilm can be maintained in equilibrium because the microorganisms in the biofilm will maintain itself only up to the layer where the gas is available.

The membranes can be configured into typical modules as shown in FIG. 4 for hollow fibers. The gas flows in the fine fibers that are bundled and potted inside a cylindrical shell or vessel through which the liquid is distributed and circulated. Very high surface areas in the range of 1000 m2 to 5000 m2 per m3 can be achieved in such modules.

The bioreactor modules can be operated in multiple stages of fermentation using the modules in counter-current, co-current or a combination thereof mode between the gas and the liquid. In the arrangement as shown in FIG. 4 a counter current operation is depicted.

During the bioconversion excess $CO_2$ is generated and this gas can diffuse back and dilute out the concentrations of CO and $H_2$ in the feed gas and thus reduce their mass transfer rates. Other types of membranes that preferentially permeate $CO_2$ over CO and $H_2$ can be used in the multi-stage configuration as shown as an example in FIG. 5 where, using a membrane that selectively permeates $CO_2$ and then returning the syngas enriched in CO and $H_2$ to the bioreactor can be achieved.

Figure 5:
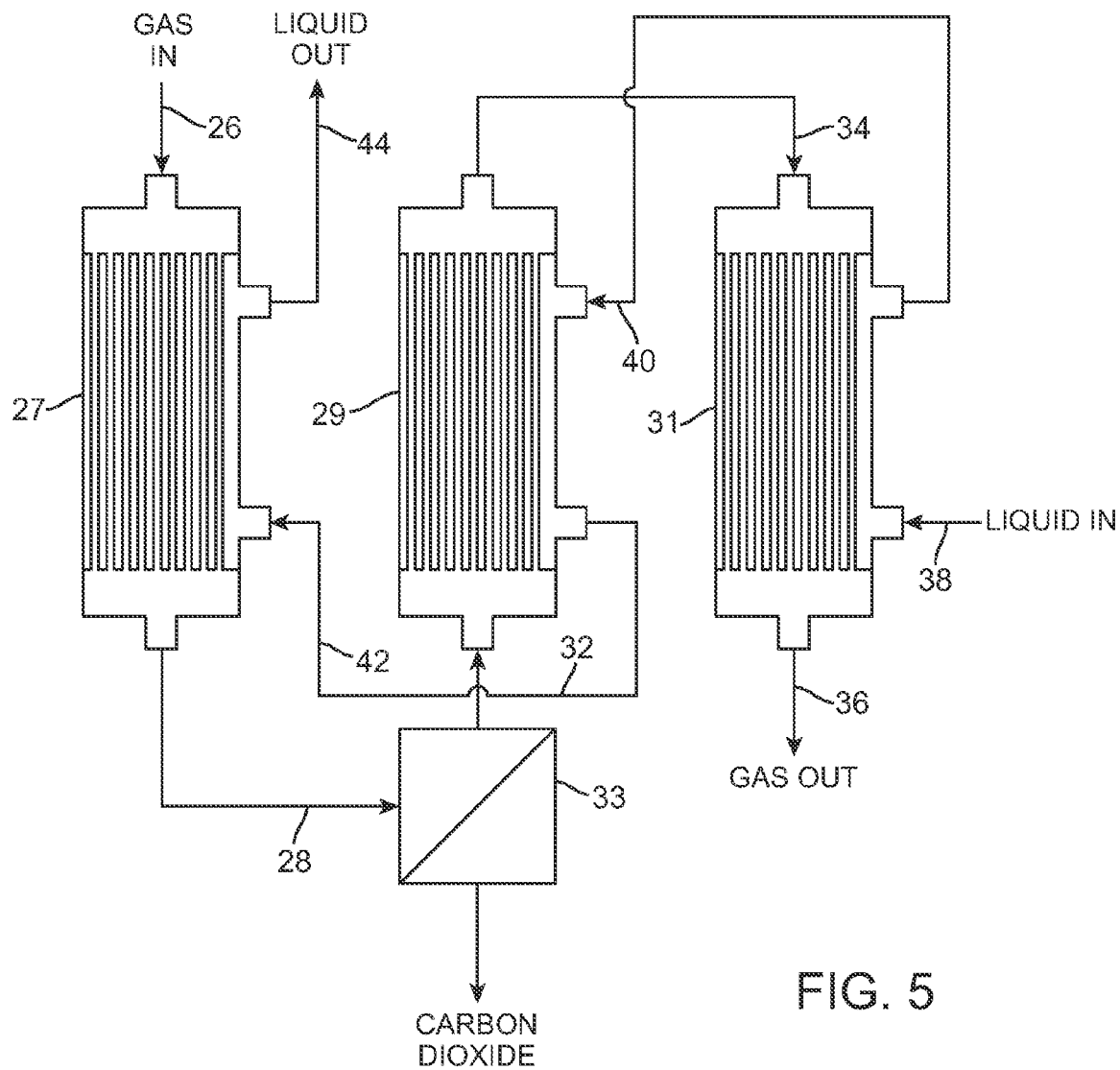
FIG. 5 is a schematic drawing showing a bioreactor system with multiple bioreactors arranged in series having intermediate carbon dioxide removal.

FIG. 5 depicts a system where the entering feed gas flows into bioreactor 27 via line 26 and serially through bioreactors 29 and 31 via lines 28, 32 and 34. At the same time liquid that contacts the biofilm layers enters the system via line 38 and flows countercurrently, with respect to the gas flow, through bioreactors 31, 29 and 27 via lines 40 and 42. Liquid products are recovered from the liquid flowing out of line 44 and gas stream is withdrawn from the system via line 36. Separation unit 33 provides the stream of line 28 with intermediate removal of $CO_2$ from the system via any suitable device or process such as a membrane or extraction step. Interconnecting lines 32 and 34 also provide the function of establishing continuous communication through all of the lumens of the different bioreactors so that any combined collection and distribution chambers provide a continuous flow path.

Figure 6:
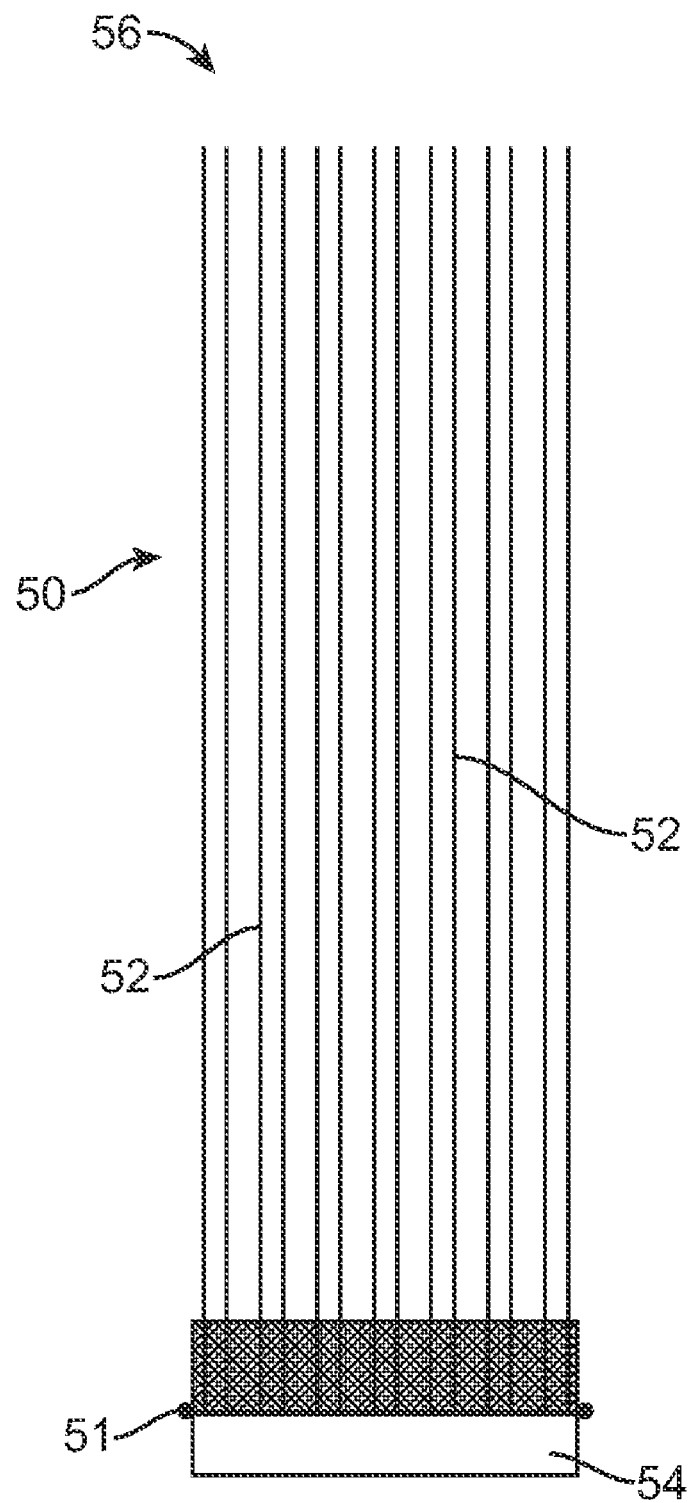
FIG. 6 is a schematic drawing of a one-headed membrane module for use in a bioreactor system with gas and liquid circulation.
Figure 7A:
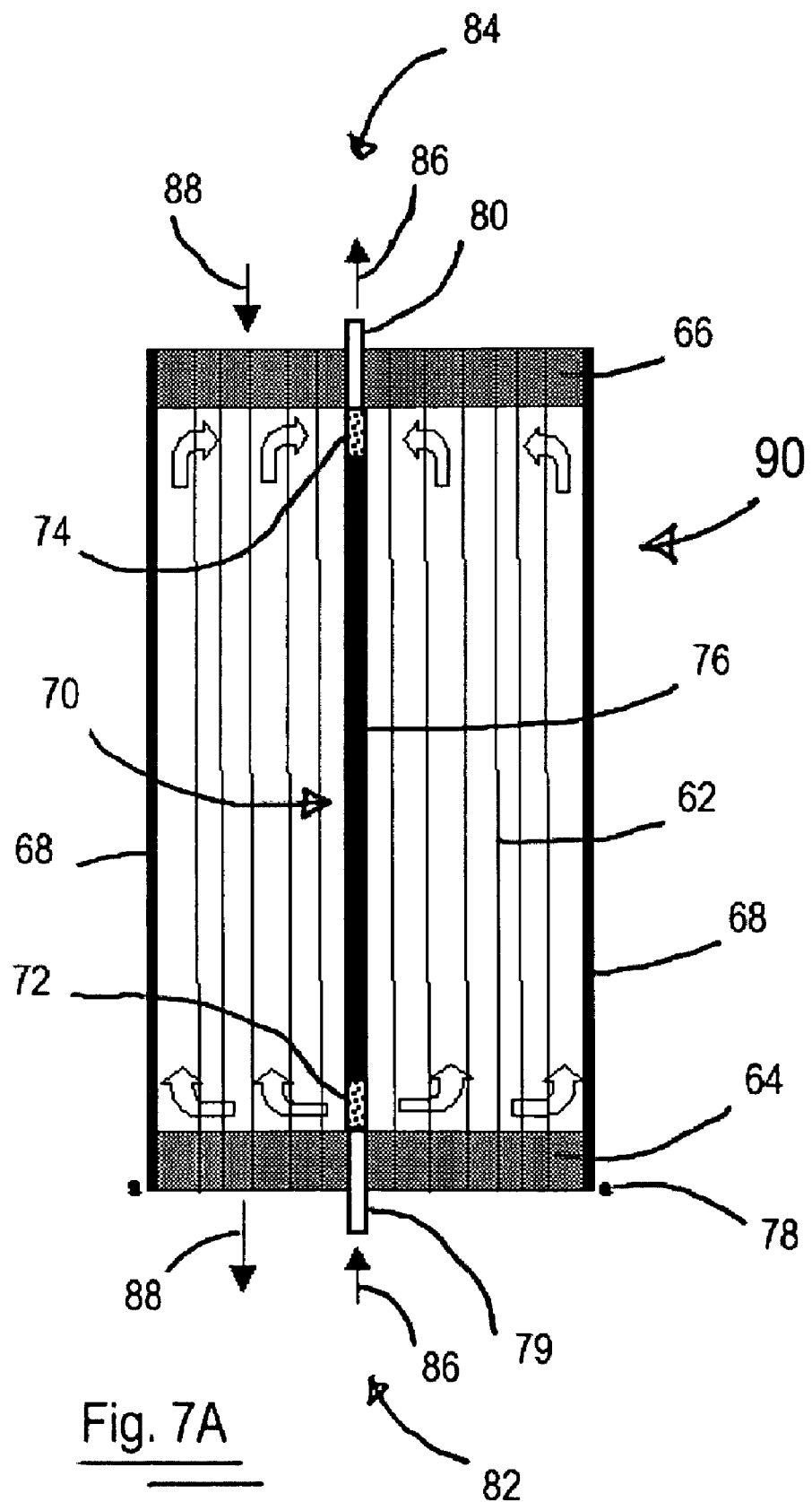
FIGS. 7A and 7B are schematic drawings of two-headed membrane modules for use in a bioreactor system with gas and liquid circulation.
Figure 7B:
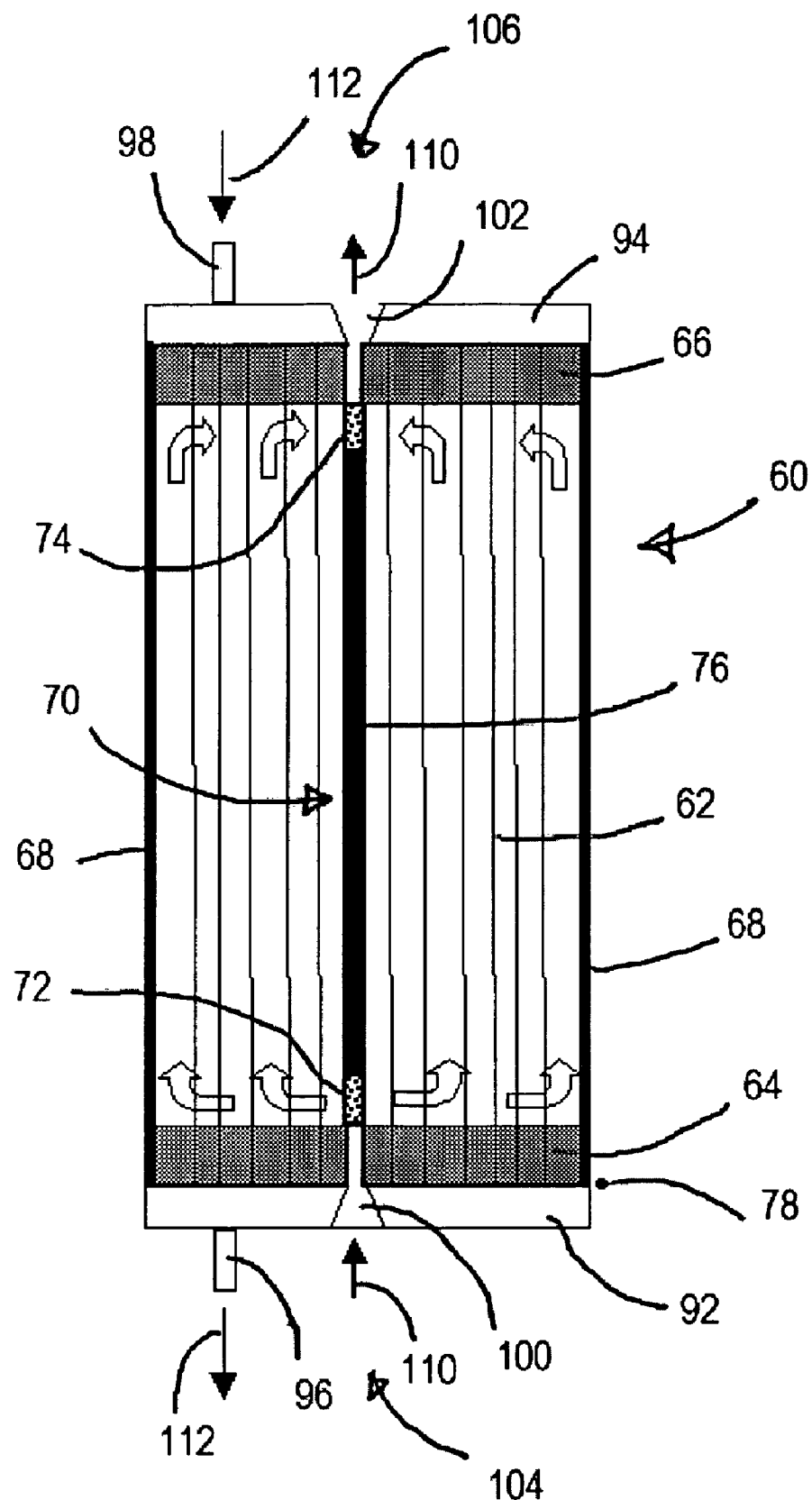

FIG. 6 and FIGS. 7A and 7B are schematic drawings of one-headed and two-headed membrane modules, respectively, for use in a bioreactor system with gas and liquid circulation. The membrane module provides a large surface area of gas-permeable membranes in the form of microporous and/or nonporous hollow fibers. A number of the membrane modules can be located in series in process liquid contained in a pressurized membrane vessel, so that a very large total membrane surface area can be achieved with a small number of membrane vessels, simplifying plant design and reducing costs. The membranes forming the hollow fibers can be gas-permeable microporous and/or nonporous membranes. In one embodiment, process gas fills the hollow fiber lumens, while biofilm and process liquid are on the shell side of hollow fibers. In one embodiment, the membrane module can have support structures around the hollow fibers to keep the hollow fibers from collapsing. The membrane module can be designed to provide a desired distribution of flow of the process liquid about individual hollow fibers and/or small bundles of hollow fibers. In one embodiment, the membrane module has a round cross section.

The membrane vessel encapsulating the membrane module and process liquid can be pressurized to increase the process gas transfer rate through the hollow fiber walls. In one embodiment, the membrane vessel is pressurized in the range of 15 to 100 psig. The membrane vessel can be a pressure vessel such as those used in water desalination plants for reverse osmosis (RO) membranes. These RO pressure vessels are commercially available from a number of manufacturers in standardized sizes and pressure ratings. The RO pressure vessels can be made of fiber reinforced plastic (FRP) composite materials for maximum operating pressures ranging from 150 psig to 1250 psig. In one embodiment, the membrane vessel for use with a membrane module is a RO pressure vessel having a maximum operating pressure of 150 psig, a diameter of 16 or 18 inches, and a length of 4 meters.

Commercially available RO pressure vessels have various diameters, such as 4, 8, 16, and 18 inches, as well as various lengths from about 1.5 meters to 7.5 meters. In one embodiment, the vessel cross sectional area perpendicular to the axis of the membrane vessel is no more than 1.5 times the cross sectional area of the membrane module. In another embodiment, the vessel cross sectional area perpendicular to the axis of the membrane vessel is between 1.2 and 1.5 times the cross sectional area of the membrane module. In one embodiment, the vessel diameter of the membrane vessel is no more than 1.25 times the diameter of the membrane module. In another embodiment, the vessel diameter of the membrane vessel is between 1.1 and 1.25 times the diameter of the membrane module. RO pressure vessels are widely available and reasonably priced, making them attractive for use as membrane vessels to reduce lead times and construction costs.

The membrane module has a number of hollow fibers and each of the hollow fibers has a hollow fiber wall defining a hollow fiber lumen and an outer surface. A process gas is disposed in the hollow fiber lumens and a biofilm is disposed on the outer surface of the hollow fibers. Process gas passes through the hollow fiber wall to interact with the biofilm and generate a liquid product that mixes with the process liquid. The process gas can be a synthesis gas (syngas), such as a mix of CO, $H_2$ and $CO_2$ with other components such as $CH_4$, $N_2$, $NH_3$, $H_2S$ and other trace gases, or the like. The biofilm supports a culture, such as *Clostridium ragsdalei, Butyribacterium methylotrophicum, Clostridium ljungdahlii, Clostridium carboxidivorans*, combinations thereof, and the like, which can generate the liquid product from the syngas. The liquid product can be ethanol, n-butanol, hexanol, acetic acid, butyric acid, combinations thereof, or the like, depending on the syngas and culture selected. Those skilled in the art will appreciate that numerous combinations of syngas and culture can be selected as desired for generating a particular liquid product desired.

FIG. 6 illustrates a one-headed membrane module. In this arrangement, the membrane module 50 includes a number of hollow fibers 52, each having a hollow fiber wall defining a hollow fiber lumen and an outer surface. A gas inlet chamber 54 is operably connected to the hollow fibers 52 to provide the process gas to the hollow fiber lumens. The hollow fibers 52 can be potted to the gas inlet chamber 54 with an epoxy or the like. The free ends 56 of the hollow fibers 52 are allowed to move freely. In one embodiment, the free ends 56 of the hollow fibers 52 can be loosely enclosed in netting (not shown) to facilitate handling of the membrane module 50 during installation or maintenance. In one embodiment, the free ends 56 of the hollow fibers 52 are open-ended, allowing gas flow from the free ends 56. In another embodiment, the hollow fibers 52 are closed-ended, hereby defined to mean preventing gas flow from and liquid backflow into the free ends 56 apart from permeation through the wall of the fibers 52. A mechanical seal 51, such as an O-ring or the like, located around the membrane module 50 helps secure and stabilize the membrane module 50 in the membrane vessel.

FIGS. 7A and 7B, in which like elements share like reference numbers, illustrate two-headed membrane modules. In these arrangements, the membrane modules 90, 60 include a number of hollow fibers 62, each having a hollow fiber wall defining a hollow fiber lumen and an outer surface. A bottom potted end 64 is operably connected to one end of the hollow fibers 62 and a top potted end 66 is operably connected to the other end of the hollow fibers 62, so that the process gas can flow through one of the potted ends, through the hollow fiber lumens, and through the other one of the potted ends. The hollow fibers 62 can be potted to the bottom potted end 64 and the top potted end 66 with an epoxy or the like. A number of support rods 68 connect the bottom potted end 64 and the top potted end 66 to provide mechanical strength to the membrane module, which must withstand forces caused by buoyancy of the hollow fibers, weight of the hollow fibers and biofilm, membrane module handling, and the like.

The hollow fibers can be oriented vertically or horizontally. For the one-headed arrangement of FIG. 6A a vertical orientation with the fibers potted at the bottom is particularly useful since it maintains the fibers in the desired position and avoids displacement due to gravity and buoyancy forces. The two headed arrangement of FIGS. 7A and 7B provide more support to the fibers and facilitates their use in a horizontal as well as vertical orientation.

In FIGS. 7A and 7B, the length of the hollow fibers 62 can be greater than the distance between the bottom potted end 64 and the top potted end 66 to give the hollow fibers 62 some slack and freedom to move. In one embodiment, the length of the hollow fibers have a length equal to 1.015 to 1.15 times the distance between the bottom potted end 64 and the top potted end 66. In another embodiment, the length of the hollow fibers have a length of equal to 1.01 to 1.15 times the distance between the bottom potted end 64 and the top potted end 66. A mechanical seal 78, such as an O-ring or the like, located around the membrane module helps secure and stabilize the membrane module in the membrane vessel. The mechanical seal 78 also prevents process liquid or process gas from bypassing the membrane module.

A tube 70 runs the length of the membrane module between the bottom potted end 64 and the top potted end 66, passing through both the bottom potted end 64 and the top potted end 66. The tube 70 includes a bottom perforated section 72 near the bottom potted end 64, a top perforated section 74 near the top potted end 66, and a blocked section 76 between the bottom perforated section 72 and the top perforated section 74. In this arrangement as indicated by the hollow arrows, process liquid in the tube 70 passes through the bottom potted end 64 and out the bottom perforated section 72, along the outer surfaces of the hollow fibers 62, in the top perforated section 74 and through the top potted end 66. The middle section 76 of the tube 70 is blocked, so that the flow of the process liquid follows the outer surfaces of the hollow fibers 62. The perforated sections of the tube 70 allows the process liquid to distribute radially about the hollow fibers 62 once the process liquid passes through the potted end. The tube primarily functions to distribute and collect liquid from the fibers 62 about central area of the potted ends 64 and 66 and can also serve as a central support between the potted ends. If central support is not needed, the continuous tube may be replaced with simple distributors and collectors.

Those skilled in the art will appreciate that the process liquid flow through the membrane module can follow flow paths instead of or in addition to the flow path through the tube 70. In one embodiment, grooves about the periphery of the membrane module at the potted ends allow supplemental flow between the membrane vessel and the membrane module in addition to the flow through the tube 70. In another embodiment, grooves about the periphery of the membrane module at the potted ends allow flow between the membrane vessel and the membrane module, but the tube is not present or no flow is allowed through the tube 70.

In the arrangements depicted by FIGS. 7A and 7B, the membrane modules are countercurrent flow membrane modules: the process liquid enters the bottom of the membrane module and exits the top, and the process gas enters the top of the membrane module and exits the bottom. Those skilled in the art will appreciate that the membrane modules can be countercurrent flow or concurrent flow, with the process liquid or process gas entering the top or the bottom of the membrane module, as desired for a particular application.

As illustrated in FIG. 7A, bottom liquid connection 79 and top liquid connection 80 are connected to or part of the tube 70 where the tube 70 passes through the bottom potted end 64 and the top potted end 66, respectively. The liquid connections 79, 80 can be attached to piping that passes out of the membrane vessel or can be attached to liquid connections of adjacent membrane modules when a number of membrane modules are connected in series within a membrane vessel. The hollow fibers 62 pass through the potted ends 64, 66, so that the hollow fiber lumens are open to bottom space 82 and top space 84. The bottom space 82 and top space 84 can be in communication with piping that passes out of the membrane vessel or adjacent membrane modules when a number of membrane modules are connected in series within a membrane vessel. In this arrangement, process liquid enters the membrane module 90 at the bottom liquid connection 79 and exits the membrane module 90 at the top liquid connection 80, as indicated by the arrows 86. Also in this arrangement, process gas enters the membrane module 90 at the bottom potted end 64 and exits the membrane module 90 at the top potted end 66, as indicated by the arrows 88.

As illustrated in FIG. 7B, the hollow fibers 62 pass through the potted ends 64, 66, so that the hollow fiber lumens are open to gas outlet chamber 92 and gas inlet chamber 94. The gas inlet chamber 92 is connected to bottom gas connection 96 and the gas outlet chamber 94 is connected to the top gas connection 98. The gas connections 96, 98 can be attached to piping that passes out of the membrane vessel or can be attached to gas connections of adjacent membrane modules when a number of membrane modules are connected in series within a membrane vessel. Bottom liquid port 100 and top liquid port 102 are connected to or part of the tube 70 where the tube 70 passes through the gas inlet chamber 92 and the gas outlet chamber 94, respectively. The bottom liquid port 100 and top liquid port 102 communicate with bottom space 104 and top space 106, respectively. The liquid ports can be shaped as desired to reduce the pressure drop across the liquid ports. The bottom space 104 and top space 106 can be in communication with piping that passes out of the membrane vessel or with adjacent membrane modules when a number of membrane modules are connected in series within a membrane vessel. In this arrangement, process liquid enters the membrane module 60 at the bottom liquid port 100 and exits the membrane module 60 at the top liquid port 102, as indicated by the arrows 110. Also in this arrangement, the process gas enters the membrane module 60 at the top gas connection 98 and exits the membrane module 60 at the bottom gas connection 96, as indicated by the arrows 112.

Figure 8:
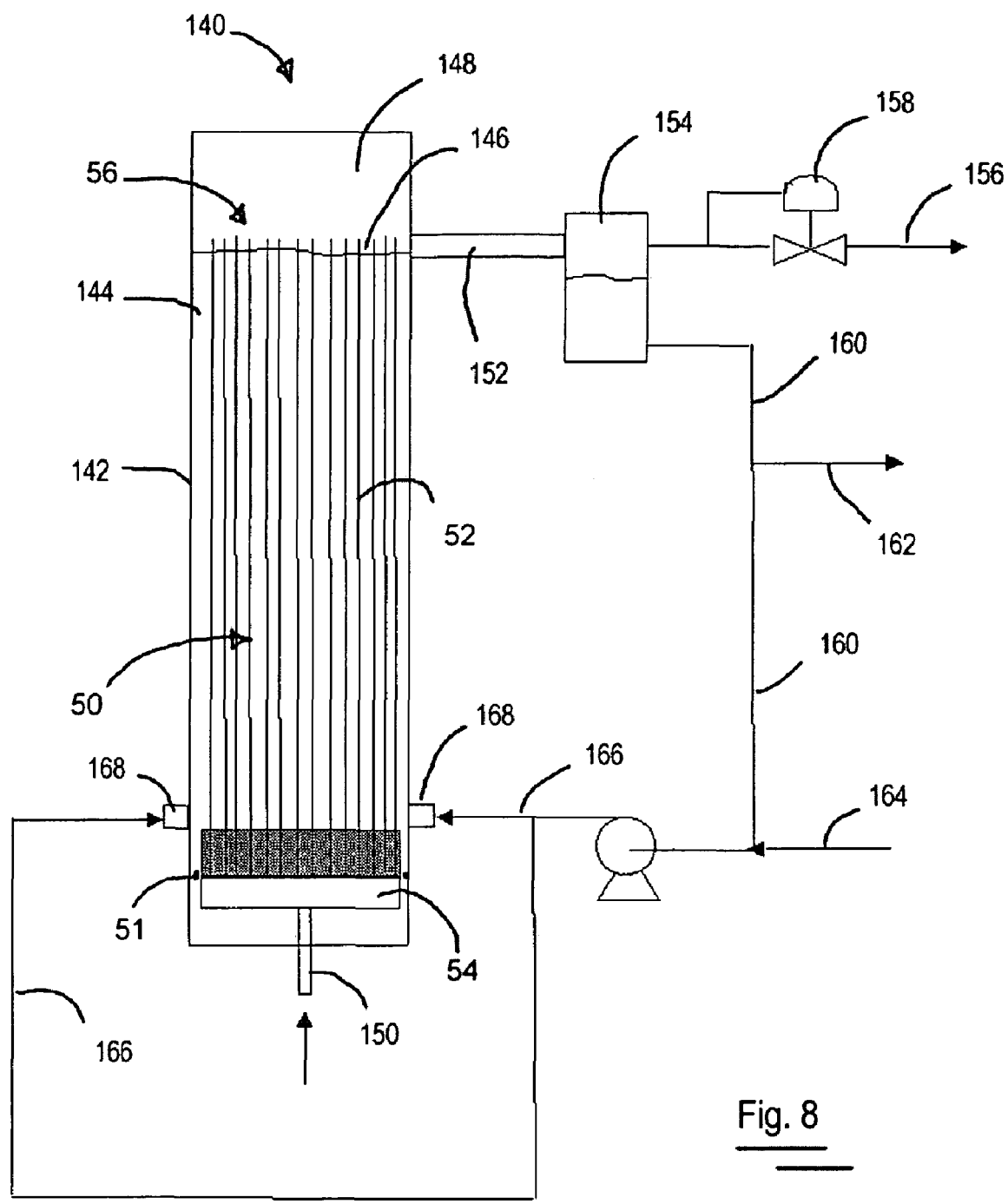
FIG. 8 is a schematic drawing of a modular membrane supported bioreactor with a one-headed membrane module.

FIG. 8, in which like elements share like reference numbers with FIG. 6, is a schematic drawing of a modular membrane bioreactor with a one-headed membrane module. In this embodiment, the membrane module 50 is a one-headed membrane module as described further for FIG. 6 with gas inlet chamber 54 operably connected to the hollow fibers 52 to provide process gas to hollow fiber lumens. Referring to FIG. 8, the free ends 56 of the hollow fibers 52 of the membrane module 50 are above the liquid surface 146. The modular membrane bioreactor 140 includes a membrane vessel 142, process liquid 144 disposed in the membrane vessel 142 and having a liquid surface 146, and a membrane module 50 at least partially submerged below the liquid surface 146. The membrane module 50 has a number of hollow fibers 52 and each of the hollow fibers 52 has a hollow fiber wall defining a hollow fiber lumen and an outer surface. A mechanical seal 51, such as an O-ring or the like, located around the membrane module 50 helps secure and stabilize the membrane module 50 in the membrane vessel 142. A process gas is disposed in the hollow fiber lumens and a biofilm is disposed on the outer surface of the hollow fibers 52. Process gas passes through the hollow fiber wall to interact with the biofilm and generate a liquid product that mixes with the process liquid. In this arrangement, the free ends 56 of the hollow fibers 52 extend above the liquid surface 146 into a headspace 148, so the free ends 56 can be open-ended or closed-ended.

A process gas, such as syngas or the like, enters the membrane vessel 142 through gas inlet 150 and enters the gas inlet chamber 54 of the membrane module 50. The process gas is distributed from the gas inlet chamber 54 into the hollow fiber lumen of each hollow fiber 134. As the process gas flows along the length of the hollow fibers 52, the process gas passes through the hollow fiber wall of the hollow fibers 52 and generates liquid product, such as ethanol or the like, through interaction with the biofilm on the outer surface of the hollow fibers 52. The liquid product mixes into and moves through the process liquid 144 by diffusion and convection. Residual process gas exits the free ends 56 of the hollow fibers 52 into the headspace 148 of the membrane vessel 142. The gas inlet 150 and gas inlet chamber 54 provide a gas supply conduit operably connected to the hollow fibers 52 for supplying a process gas to the hollow fiber lumens.

An overflow conduit 152 at the liquid surface 146 is connected to the membrane vessel 142 to receive exhaust gas and the process liquid. A gas/liquid separation tank 154 is connected to the overflow conduit 152 to separate the exhaust gas from the process liquid. The overflow conduit 152 controls the liquid level in the membrane vessel 142 at a predetermined level and allows process liquid and exhaust gas to flow from the membrane vessel 142 to the gas/liquid separation tank 154, from which the exhaust gas exits the gas/liquid separation tank 154 through an exhaust outlet 156. A pressure control valve 158 responsive to sensed membrane vessel pressure can be connected to the membrane vessel 142 above the liquid surface 146 to control the pressure in the membrane vessel 142 at a desired value, such as in the range of 15 to 100 psig, to increase the process gas transfer rate through the hollow fiber walls. In one embodiment, the pressure control valve 158 is operably connected to the exhaust outlet 156, such as connection through the gas/liquid separation tank 154.

In one embodiment, the modular membrane bioreactor further includes a product recovery system serving one or more modular membrane bioreactors and operably connected to receive the process liquid from the gas/liquid separation tank 154, separate liquid product from the process liquid, and return process liquid to the membrane vessel 142. The process liquid including liquid product passes from the gas/liquid separation tank 154 in a recirculation stream 160. At least a portion of the recirculation stream 160 is drawn off as product stream 162 for recovery of the liquid product from the process liquid. The recirculation stream 160 is mixed with a recycle stream 164 including fresh liquid and/or recycled broth, i.e., process liquid at least partially stripped of the liquid product, to form a feed stream 166 of feed liquid which is pumped into the membrane vessel 142 at the liquid inlet ports 168 of the membrane vessel 142. The position of the liquid inlet port 168 can be selected to provide a desired distribution of flow of the process liquid 144 about individual hollow fibers 52 and/or small bundles of hollow fibers 52. Those skilled in the art will appreciate that a number of membrane vessels can be connected in parallel so that a single process gas header feeds a number of membrane modules.

Figure 9:
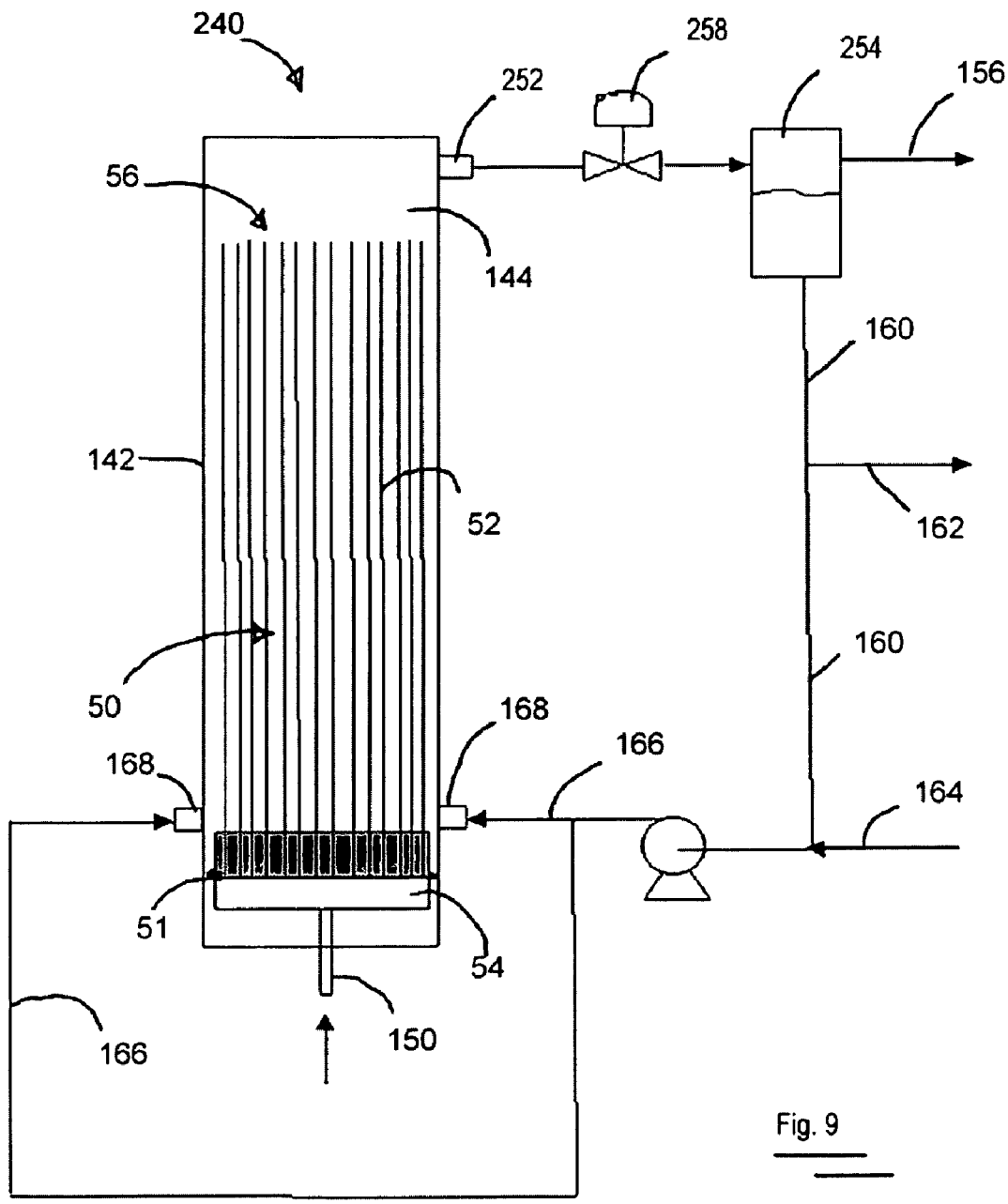
FIG. 9 is a schematic drawing of another embodiment of a modular membrane bioreactor with a one-headed membrane module.

FIG. 9, in which like elements share like reference numbers with FIGS. 6 and 8, is a schematic drawing of another embodiment of a modular membrane bioreactor with a one-headed membrane module. In this embodiment, the membrane module 50 is a one-headed membrane module as described further for FIG. 6 with gas inlet chamber 54 operably connected to the hollow fibers 52 to provide the process gas to hollow fiber lumens. Referring to FIG. 9, the free ends 56 of the hollow fibers 52 of the membrane module 50 are submerged in the process liquid which fills the membrane vessel 142. The modular membrane bioreactor 240 includes a membrane vessel 142, process liquid 144 disposed in the membrane vessel 142, and a membrane module 50 submerged in the process liquid 144. In this arrangement, the free ends 56 of the hollow fibers 52 submerged in the process liquid 144, so the free ends 56 are closed-ended.

A liquid outlet 252 is connected to the membrane vessel 142 to receive the process liquid including liquid product and dissolved residual process gases. A gas/liquid separation tank 254 is connected to the liquid outlet 252 to separate the exhaust gas from the process liquid. A pressure reducing valve 258 between the liquid outlet 252 and the gas/liquid separation tank 254 allows a portion of the dissolved gases in the process liquid saturated with the dissolved residual process gases to be released due to the pressure reduction. The pressure reducing valve 258 can serve one or more modular membrane bioreactors.

The pressure reducing valve 258 can assist in controlling the pressure in the membrane vessel 142 at a desired value, such as in the range of 15 to 100 psig, to increase the process gas transfer rate through the hollow fiber walls. Exhaust gas exits the gas/liquid separation tank 254 through an exhaust outlet 256. In one embodiment, the modular membrane bioreactor further includes a product recovery system serving one or more modular membrane bioreactors and operably connected to receive the process liquid in a recirculation stream 160 from the gas/liquid separation tank 254.

Figure 10:
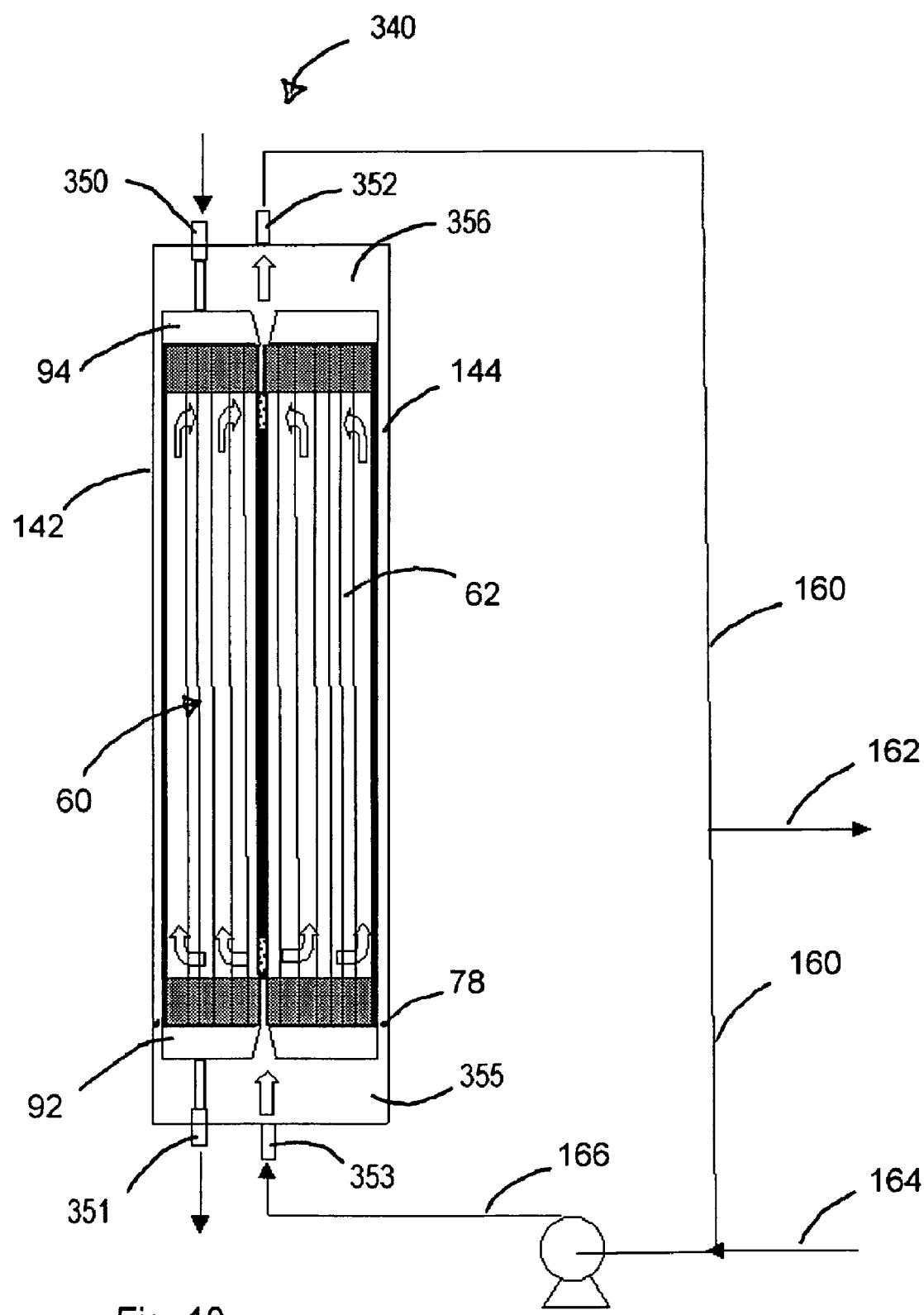
FIG. 10 is a schematic drawing of a modular membrane supported bioreactor with a two-headed membrane module.

FIG. 10, in which like elements share like reference numbers with FIGS. 7B and 8, is a schematic drawing of a modular membrane supported bioreactor with a two-headed membrane module. In this embodiment, the membrane module 60 is a two-headed membrane module as described further for FIG. 7B having a gas inlet chamber 94 and a gas outlet chamber 92. Referring to FIG. 10, the gas inlet chamber 94 and the gas outlet chamber 92 are operably connected to the hollow fibers 62 to allow the process gas to flow through the hollow fiber lumens from the gas inlet chamber 94 to the gas outlet chamber 92.

The modular membrane bioreactor 340 includes a membrane vessel 142, process liquid 144 disposed in the membrane vessel 142, and a membrane module 60 submerged in the process liquid 144. The membrane vessel 142 can be pressurized to a desired pressure, such as a pressure in the range of 15 to 100 psig.

A process gas, such as syngas or the like, enters the membrane vessel 142 through gas inlet 350 and enters the gas inlet chamber 94 of the membrane module 60. The process gas is distributed from the gas inlet chamber 94 into the hollow fiber lumen of each hollow fiber 62. As the process gas flows along the length of the hollow fibers 62, the process gas passes through the hollow fiber wall of the hollow fibers 62 and generates liquid product, such as ethanol or the like, through interaction with the biofilm on the outer surface of the hollow fibers 62. The liquid product mixes into and moves through the process liquid 144 by diffusion and convection. The process gas enters the gas outlet chamber 92 on exiting the hollow fibers 62 and exits the membrane vessel 142 through gas outlet 351. The gas inlet 350 and gas inlet chamber 94 provide a gas supply conduit operably connected to the hollow fibers 62 for supplying a process gas to the hollow fiber lumens.

A liquid outlet 352 is connected to the membrane vessel 142 to receive the process liquid including liquid product, which leaves the membrane module 60 and passes through the liquid outlet plenum 356 between the membrane vessel 142 and the membrane module 60. In one embodiment, the modular membrane bioreactor further includes a product recovery system serving one or more modular membrane bioreactors and operably connected to receive the process liquid from the liquid outlet 352 in a recirculation stream 160. Feed stream 166 of feed liquid is pumped into the membrane vessel 142 at the liquid inlet 353 of the membrane vessel 142. The feed liquid enters the membrane module 60 after passing through the liquid inlet plenum 355 between the membrane vessel 142 and the membrane module 60.

Those skilled in the art will appreciate that a number of variations are possible for a modular membrane supported bioreactor with a two-headed membrane module. In one embodiment, the two-headed membrane module is a two-headed membrane module as described for FIG. 7B and illustrated in FIG. 10. In another embodiment, the two-headed membrane module is a two-headed membrane module as described for FIG. 7A, with the process gas filling the inlet and outlet plenums of the membrane vessel. In one embodiment, the process gas flow and process liquid flow are countercurrent flows as illustrated in FIG. 10. In another embodiment, the process gas flow and process liquid flow are concurrent flows. In one embodiment, the gas outlet can be closed to maximize gas utilization efficiency, so that the hollow fibers perform as if the hollow fibers are closed ended.

Figure 11:
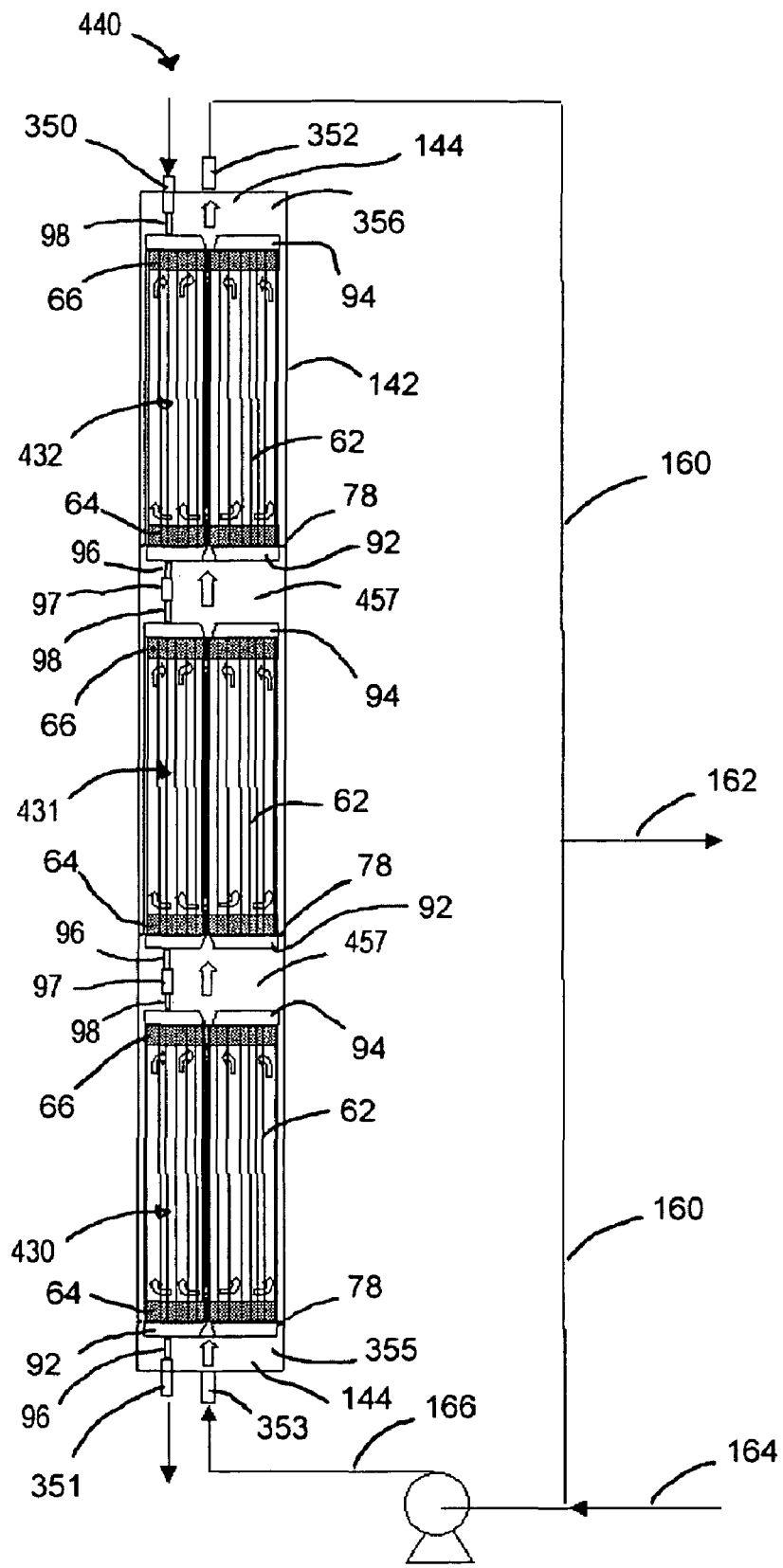
FIG. 11 is a schematic drawing of another embodiment of a modular membrane supported bioreactor with two-headed membrane modules.

FIG. 11, in which like elements share like reference numbers with FIGS. 7B, 8, and 10, is a schematic drawing of another embodiment of a modular membrane supported bioreactor with two-headed membrane modules. In this embodiment, the membrane module is an axial stack of membrane modules 430, 431, 432, which are two-headed membrane modules as described further for FIG. 7B. Referring to FIG. 11, the membrane modules are connected in series between the liquid inlet plenum 355 and the liquid outlet plenum 356, with liquid intermediate plenums 457 between the membrane modules and intermediate connectors 97 joining the gas outlet 96 of one membrane module to the gas inlet 98 of the adjacent membrane module.

The membrane modules 430, 431, 432 have top potted ends 66 connected to gas inlet chambers 94 and bottom potted ends 64 connected to gas outlet chambers 475. The top potted end 66 is connected to one end of the hollow fibers 62 and the bottom potted end 64 is connected to the other end of the hollow fibers 62 to allow the process gas to flow through the hollow fiber lumens from the top potted end 66 to the bottom potted end 64. The process gas from the hollow fiber lumens of one two-headed membrane module flows through the hollow fiber lumens of the other two-headed membrane modules and the process liquid about the outer surface of the hollow fibers of one two-headed membrane module flows about the outer surface of the hollow fibers of the other two-headed membrane modules. That is, the process gas and the process liquid flow through all the membrane modules 430, 431, 432. In one embodiment, the relative flow between the process gas and process liquid is countercurrent flow as illustrated. In another embodiment, the relative flow between the process gas and process liquid is concurrent flow.

A process gas, such as syngas or the like, enters the membrane vessel 142 through gas inlet 350 and enters the gas inlet chamber 94 of the top membrane module 432 through the top gas connection 98. The process gas is distributed from the gas inlet chamber 94 into the hollow fiber lumen of each hollow fiber 62 through the top potted end 66. As the process gas flows along the length of the hollow fibers 62, the process gas passes through the hollow fiber wall of the hollow fibers 62 and generates liquid product, such as ethanol or the like, through interaction with the biofilm on the outer surface of the hollow fibers 62. The liquid product mixes into the process liquid 144 by diffusion and convection. The process gas exits the top membrane module 432 through the bottom gas connection 96 attached to the gas outlet chamber 92, passes through the intermediate connectors 97, and enters the next membrane module 431 through its top gas connection 98. The process gas continues through the membrane modules 430 until reaching the bottom membrane module 430 and exiting the membrane vessel 142 through gas outlet 351. The gas inlet 350, top gas connection 98, and gas inlet chamber 94 provide a gas supply conduit operably connected to the hollow fibers 62 for supplying a process gas to the hollow fiber lumens. The top gas connection 98 provides a gas supply conduit for each membrane module 430, 431, 432.

Process liquid 144 enters the membrane vessel 142 through liquid inlet 353 and enters the liquid inlet plenum 355 between the membrane vessel 142 and the bottom membrane module 430. The process liquid passes about the outer surface of the hollow fibers 62 of bottom membrane module 430 and enters the liquid intermediate plenum 457 between the bottom membrane module 430 and the adjacent membrane module 431. The process liquid continues through the membrane modules until reaching the top membrane module 432 and exiting the membrane vessel 142 through liquid outlet plenum 356 and liquid outlet 352.

The liquid outlet 352 is connected to the membrane vessel 142 to receive the process liquid including liquid product. In one embodiment, the modular membrane bioreactor further includes a product recovery system serving one or more modular membrane bioreactors and operably connected to receive the process liquid from the liquid outlet 352 in a recirculation stream 160. Feed stream 166 of feed liquid is pumped into the membrane vessel 142 at the liquid inlet 353 of the membrane vessel 142. The feed liquid enters the membrane module 430 after passing through the liquid inlet plenum 355 between the membrane vessel 142 and the membrane module 430.

The connection at the intermediate connectors 97 can be made using a number of methods, such as standard pipe-threaded fittings, compression fittings, flanges, sanitary fittings, and the like. The membrane modules can be connected to minimize the size of the liquid intermediate plenums 457. One arrangement using O-rings and sliding seals is described in U.S. Pat. No. 5,851,267, incorporated herein by reference.

Those skilled in the art will appreciate that a number of variations are possible for a modular membrane supported bioreactor with two-headed membrane modules. In one embodiment, the two-headed membrane modules are two-headed membrane modules as described for FIG. 7B and illustrated in FIG. 11. In another embodiment, the two-headed membrane modules are two-headed membrane modules as described for FIG. 7A, with the process gas filling the plenums between adjacent membrane modules and the process liquid being piped from one membrane module to the adjacent membrane module. In one embodiment, a process liquid conduit communicates the process liquid from one membrane module to an adjacent membrane module. In one embodiment, the process gas flow and process liquid flow are countercurrent flows as illustrated in FIG. 11. In another embodiment, the process gas flow and process liquid flow are concurrent flows. In one embodiment, the gas outlet can be closed to maximize gas utilization efficiency, so that the hollow fibers perform as if the hollow fibers are closed ended.

The growing of a biofilm in the various embodiments of this invention can include growing a biofilm supporting a culture selected from the group consisting of *Clostridium ragsdalei, Butyribacterium methylotrophicum, Clostridium ljungdahlii, Clostridium carboxidivorans*, and combinations thereof. The anaerobic acetogenic bacteria, *Clostridium carboxidivorans* has all of the identifying characteristics of ATCC no. BAA-624; can be used and this will enable the production of ethanol, n-butanol and acetic acid. The anaerobic bacteria *Butyribacterium methylotrophicum*, has the identifying characteristics of ATCC 33266 and can be adapted to CO use to enable the production of n-butanol as well as butyric acid. The anaerobic bacteria *Clostridium ljungdahlii*, has the identifying characteristics of ATCC 55988 and 55989 can be used to enable the production of ethanol as well as acetic acid.

EXAMPLE

A Liqui-Cel® membrane contactor MiniModule® 1×5.5 from Membrana (Charlotte, N.C.) is used as a membrane supported bioreactor for the conversion of carbon monoxide and hydrogen into ethanol. This membrane module contains X50 microporous hydrophobic polypropylene hollow fibers with 40% porosity and 0.04 μm pore size. The fiber outer diameter is 300 μm and internal diameter 220 μm. The active membrane surface area of the module is 0.18 m². A gas containing 40% CO, 30% $H_2$, and 30% $CO_2$ is fed to the lumen of the fibers at 60 std ml/min and 2 psig inlet pressure and the residual gas exits the module at 1 psig outlet pressure. The membrane module is connected to a 3-liter BioFlo® 110 Fermentor from New Brunswick Scientific (Edison, N.J.). The fermentation medium having the composition given in Table 2 is pumped from the fermentor, flows through the shell side of the membrane module, and returns to the fermentor. The flow rate of this recirculating medium is 180 ml/min, and the pressure at the outlet of the membrane module is maintained at 5 psig by adjusting a back-pressure valve. The fermentor contains 2 liters of the fermentation medium, which is agitated at 100 rpm and maintained at 37° c. The fermentor is maintained under anaerobic conditions.

The fresh fermentation medium contains the components listed in Tables 2 & 3(a)-(d). Initially, the bioreactor system is operated in the batch mode and inoculated with 200 ml of an active culture of *Clostridium ragsdalei* ATCC No. BAA-622. The fermentation pH is controlled at pH 5.9 in the first 24 hours by addition of 1 N $NaHCO_3$ to favor cell growth and then allowed to drop without control until it reaches pH 4.5 to favor ethanol production. The system remains in the batch mode for 10 days to establish the attachment of the microbial cells on the membrane surface. Then, the system is switched to continuous operation, with continuous withdrawal of the fermentation broth for product recovery and replenish of fresh medium. With the continuous operation, suspended cells in the fermentation broth are gradually removed from the bioreactor system and decrease in concentration, while the biofilm attached on the membrane surface continues to grow until the biofilm reaches a thickness equilibrated with the operating conditions. The ethanol concentration at the end of the 10-day batch operation is 5 g/L. At the beginning of the continuous operation, a low broth withdrawal rate is selected so that the ethanol concentration in the broth does not decrease but increases with time. The broth withdrawal rate is then gradually increased. After 20 days of continuous operation, the ethanol concentration increases to 10 g/L with the broth withdrawal rate at 20 ml/hr.

TABLE 2

Fermentation Medium Compositions

| Components | Amount per liter |
|---|---|
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 6.1 |
| Reducing agent, See Table 2(d) | 2.5 ml |

TABLE 3(a)

Mineral Solution

| Components | Concentration (g/L) |
|---|---|
| NaCl | 80 |
| NH$_4$Cl | 100 |
| KCl | 10 |
| KH$_2$PO$_4$ | 10 |
| MgSO$_4$•7H$_2$O | 20 |
| CaCl$_2$•2H$_2$O | 4 |

TABLE 3(b)

Trace Metals Solution

| Components | Concentration (g/L) |
|---|---|
| Nitrilotriacetic acid | 2.0 |
| Adjust the pH to 6.0 with KOH | |
| MnSO$_4$•H$_2$O | 1.0 |
| Fe(NH$_4$)$_2$(SO$_4$)$_2$•6H$_2$O | 0.8 |
| CoCl$_2$•6H$_2$O | 0.2 |
| ZnSO$_4$•7H$_2$O | 1.0 |
| NiCl$_2$•6H$_2$O | 0.2 |
| Na$_2$MoO$_4$•2H$_2$O | 0.02 |
| Na$_2$SeO$_4$ | 0.1 |
| Na$_2$WO$_4$ | 0.2 |

TABLE 3(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 3(d)

Reducing Agent

| Components | Concentration (g/L) |
|---|---|
| Cysteine (free base) | 40 |
| Na$_2$S•9H$_2$O | 40 |

While the embodiments of the invention disclosed herein are presently considered to be preferred, various changes and modifications can be made without departing from the scope of the invention. The scope of the invention is indicated in the appended claims, and all changes that come within the meaning and range of equivalents are intended to be embraced therein.

The invention claimed is:

1. A modular membrane bioreactor for anaerobic conversion of gas into liquid products comprising:
a plurality of membrane modules having a plurality of hollow fibers packed across a cross sectional area of the membrane module in a direction transverse to an axis of the membrane module that extends in an axial direction, wherein said modules are stacked in said axial direction and the length of the hollow fibers extend in the axial direction of module stacking;
each of the plurality of hollow fibers in the modules have a gas permeable hollow fiber wall defining a hollow fiber lumen and an outer surface and the fibers are potted at each end of the module to provide potted ends opposite axial ends of each module;
a membrane vessel for retaining the plurality of membrane modules axially aligned within the vessel in said axial direction and at least partially submerged in a process liquid and isolated from the ambient atmosphere, the membrane vessel having a vessel cross sectional area perpendicular to the axis of the membrane vessel of no more than 1.5 times the cross sectional area of the membrane module and an inner diameter greater than the exterior diameter of the membrane modules to space the membrane vessel apart from the membrane modules;
a gas inlet at one axial end of each module adapted to supply a process gas to the lumens of the hollow fibers and a gas outlet at an axial end of the module opposite the gas inlet to withdraw process gas that together provide process gas flow through the lumens of the hollow fibers in the module;
a liquid inlet defined at least in part by one of said potted ends of each module to supply a process liquid to the hollow fibers and a liquid outlet defined at least in part by the potted end of the module opposite the liquid inlet and adapted to withdraw process liquid from the hollow fibers;
a peripheral flow path at least on end of each module defined about the periphery of its potted end and extending about the periphery of the potted end and adapted to provide liquid flow between the potted end of the module and the wall of the vessel retaining the modules, said peripheral flow path providing one of said liquid inlet or said liquid outlet for supplying or withdrawing liquid to or from the outside of the hollow fibers; and,
a gas supply conduit operably connected to the gas inlet for supplying a process gas to the hollow fiber lumens that enables the formation of a biofilm on the outer surface of the hollow fiber wall by interaction of microorganisms with the process gas and the production of a liquid product that mixes with the process liquid.

2. The bioreactor of claim 1 wherein:
the gas supply conduit is operably connected to the hollow fiber lumens to supply the process gas containing at least one of CO or a mixture of CO$_2$ and H$_2$; and,
the membrane vessel retains the membrane module(s) in the process liquid for the formation of the biofilm containing microorganisms selected from the group consisting of *Clostridium ragsdalei, Butyribacterium methylotrophicum, Clostridium ljungdahlii, Clostridium carboxidivorans*, and combinations thereof and for the production of the liquid product selected from the group consisting of ethanol, n-butanol, hexanol, acetic acid, butyric acid, and combinations thereof.

3. The bioreactor of claim 1 wherein the membrane vessel is adapted for complete filling by the process liquid.

4. The bioreactor of claim 3 further comprising:
a liquid outlet in communication with the membrane vessel to withdraw the process liquid;
a pressure reducing valve operably connected to the liquid outlet to receive the process liquid and to reduce the pressure of the process liquid to diffuse dissolved gas from the process liquid; and a gas/liquid separation tank operably connected to the pressure reducing valve to separate the diffused process gas from the process liquid.

5. The bioreactor of claim 4 further comprising a product recovery system operably connected to receive the process liquid from the gas/liquid separation tank, to separate the liquid product from the process liquid, and to return process liquid to the membrane vessel.

6. The bioreactor of claim 1 wherein the hollow fibers have a length equal to 1.015 to 1.15 times the distance between the potted ends and opposite axial ends of each module to produce slack in the fibers.

7. The bioreactor of claim 1 wherein:

a process liquid conduit communicates the process liquid from one axial end of a first membrane module to an adjacent axial end of a second membrane module;

the membrane modules further comprise a gas inlet chamber in communication with the gas inlet of each membrane module and configured for communication with the hollow fiber lumens and a gas outlet chamber in communication with the gas outlet of each membrane module and configured for communication with the hollow fiber lumens; and, the gas outlet chambers of adjacent membrane modules communicate with the gas inlet chambers of an adjacent membrane modules.

8. The bioreactor of claim 1 further comprising a tube extending between the first potted end and the second potted end, the tube having a first perforated section proximate the first potted end to disperse a portion of the liquid inlet, a second perforated section proximate the second potted end to collect a portion of the liquid outlet, and a blocked section between the first perforated section and the second perforated section to prevent fluid flow through the tube.

9. The bioreactor of claim 1 wherein: the membrane modules are in liquid communication over the entire length of the membrane vessel that extends in said axial direction to contact the outer surface of the hollow fibers in each membrane module with the process liquid.

10. The bioreactor of claim 1 wherein the diameter of the membrane vessel is from 1.1 to 1.25 times the diameter of the membrane module.

11. The bioreactor of claim 1 wherein the membrane vessel and the membrane modules define an intermediate plenum between adjacent membrane modules having a configuration that communicates process liquid between adjacent modules.

* * * * *

UNITED STATES PATENT AND TRADEMARK OFFICE
CERTIFICATE OF CORRECTION

PATENT NO. : 8,017,384 B2  Page 1 of 1
APPLICATION NO. : 12/111734
DATED : September 13, 2011
INVENTOR(S) : Shih-Perng Tsai et al.

It is certified that error appears in the above-identified patent and that said Letters Patent is hereby corrected as shown below:

Title Page, Item (73) Assignee should read:

(73) Assignee: Coskata Energy, Inc.

Signed and Sealed this
Thirteenth Day of March, 2012

David J. Kappos
*Director of the United States Patent and Trademark Office*